(12) United States Patent
Schraga

(10) Patent No.: US 7,905,898 B2
(45) Date of Patent: Mar. 15, 2011

(54) ADJUSTABLE LANCET DEVICE AND METHOD

(75) Inventor: Steven Schraga, Surfside, FL (US)

(73) Assignee: Stat Medical Devices, Inc., North Miami, FL (US)

( * ) Notice: Subject to any disclaimer, the term of this patent is extended or adjusted under 35 U.S.C. 154(b) by 66 days.

(21) Appl. No.: 10/641,142

(22) Filed: Aug. 15, 2003

(65) Prior Publication Data
US 2005/0038465 A1 Feb. 17, 2005

(51) Int. Cl.
*A61B 17/32* (2006.01)
(52) U.S. Cl. .............................................. 606/181
(58) Field of Classification Search ................. 606/182, 606/181; 600/583
See application file for complete search history.

(56) References Cited

U.S. PATENT DOCUMENTS

| | | |
|---|---|---|
| 676,678 A | 6/1901 | Ellifrits |
| 1,135,465 A | 4/1915 | Pollock |
| 2,699,784 A | 1/1955 | Krayl |
| 2,848,809 A | 2/1956 | Crowder |
| 2,823,677 A | 2/1958 | Hein, Jr. |
| 3,589,213 A | 6/1971 | Gourley |
| 3,760,809 A | 9/1973 | Campbell, Jr. |
| 4,064,871 A | 12/1977 | Reno |
| 4,139,011 A | 2/1979 | Benoit et al. |
| 4,157,086 A | 6/1979 | Maiorano et al. |
| 4,203,446 A | 5/1980 | Höfert et al. |
| 4,257,561 A | 3/1981 | McKinney |
| 4,388,925 A | 6/1983 | Burns |
| 4,426,105 A | 1/1984 | Plaquin et al. |
| 4,438,770 A | 3/1984 | Unger et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,539,988 A | 9/1985 | Shirley et al. |
| 4,553,541 A | 11/1985 | Burns |
| 4,628,929 A | 12/1986 | Intengan et al. |

(Continued)

FOREIGN PATENT DOCUMENTS

CA 523078 3/1956

(Continued)

OTHER PUBLICATIONS

Sutor et al., "Bleeding from Standardized Skin Punctures: Automated Technic for Recording Time, Intensity, and Pattern of Bleeding", *A.J.C.P.*, vol. 55, pp. 541-549 (May 1971).

*Primary Examiner* — Anhtuan T Nguyen
*Assistant Examiner* — Tuan V Nguyen
(74) *Attorney, Agent, or Firm* — Greenblum & Bernstein, P.L.C.

(57) ABSTRACT

Lancet device that includes a body. A front cover includes a skin engaging end that includes a lancet opening through which a lancet needle extends. A holding member is movably mounted within the body. The holding member includes a front end and a rear end. The front end is configured to receive a lancet. A main spring is disposed between the front and rear ends of the holding member. A first stop surface is arranged on a front portion of the holding member. A second stop surface is axially retained to a front portion of the body. At least partial rotation of the front cover causes the skin engaging end to move axially relative to the second stop surface.

45 Claims, 24 Drawing Sheets

U.S. PATENT DOCUMENTS

| | | |
|---|---|---|
| 4,643,189 A | 2/1987 | Mintz |
| 4,785,858 A | 11/1988 | Valentini et al. |
| RE32,922 E * | 5/1989 | Levin et al. ............ 606/182 |
| 4,834,667 A | 5/1989 | Fowler et al. |
| 4,858,607 A | 8/1989 | Jordan et al. |
| 4,869,249 A | 9/1989 | Crossman et al. |
| 4,895,147 A | 1/1990 | Bodicky et al. |
| 4,924,879 A | 5/1990 | O'Brien |
| 4,976,724 A | 12/1990 | Nieto et al. |
| 4,990,154 A | 2/1991 | Brown et al. |
| 5,074,872 A | 12/1991 | Brown et al. |
| 5,133,730 A | 7/1992 | Biro et al. |
| 5,147,375 A | 9/1992 | Sullivan et al. |
| 5,212,879 A | 5/1993 | Biro et al. |
| 5,269,799 A | 12/1993 | Daniel |
| 5,282,822 A | 2/1994 | Macors et al. |
| 5,304,193 A | 4/1994 | Zhadanov |
| 5,314,441 A | 5/1994 | Cusack et al. |
| 5,318,584 A | 6/1994 | Lange et al. |
| 5,324,303 A | 6/1994 | Strong et al. |
| 5,350,392 A | 9/1994 | Purcell et al. |
| 5,356,420 A | 10/1994 | Czernecki et al. |
| 5,366,470 A | 11/1994 | Ramel |
| 5,368,047 A | 11/1994 | Suzuki et al. |
| 5,395,388 A | 3/1995 | Schraga |
| 5,423,847 A | 6/1995 | Strong et al. |
| 5,439,473 A | 8/1995 | Jorgensen |
| 5,454,828 A | 10/1995 | Schraga |
| 5,464,418 A | 11/1995 | Schraga |
| 5,476,101 A | 12/1995 | Schramm et al. |
| 5,487,748 A | 1/1996 | Marshall et al. |
| 5,509,345 A | 4/1996 | Cyktich |
| 5,518,004 A | 5/1996 | Schraga |
| 5,527,333 A | 6/1996 | Nikkels et al. |
| 5,527,334 A | 6/1996 | Kanner et al. |
| 5,529,581 A | 6/1996 | Cusack |
| 5,545,174 A | 8/1996 | Schenk et al. |
| 5,554,166 A | 9/1996 | Lange et al. |
| 5,569,286 A | 10/1996 | Peckham et al. |
| 5,569,287 A | 10/1996 | Tezuka et al. |
| 5,571,132 A | 11/1996 | Mawhirt et al. |
| D376,203 S | 12/1996 | Schraga |
| 5,613,978 A | 3/1997 | Harding |
| 5,628,764 A | 5/1997 | Schraga |
| 5,628,765 A | 5/1997 | Morita |
| 5,643,306 A | 7/1997 | Schraga |
| 5,662,672 A | 9/1997 | Pambianchi et al. |
| 5,730,753 A | 3/1998 | Morita |
| 5,733,300 A | 3/1998 | Pambianchi et al. |
| 5,741,288 A | 4/1998 | Rife |
| RE35,803 E | 5/1998 | Lange et al. |
| 5,772,677 A | 6/1998 | Mawhirt et al. |
| 5,797,940 A | 8/1998 | Mawhirt et al. |
| 5,797,942 A | 8/1998 | Schraga |
| 5,873,887 A | 2/1999 | King et al. |
| 5,879,367 A | 3/1999 | Latterell et al. |
| 5,908,434 A | 6/1999 | Schraga |
| 5,916,230 A | 6/1999 | Brennenman et al. |
| 5,984,940 A | 11/1999 | Davis et al. |
| 6,010,519 A | 1/2000 | Mawhirt et al. |
| 6,022,366 A | 2/2000 | Schraga |
| 6,042,595 A | 3/2000 | Morita |
| 6,045,567 A | 4/2000 | Taylor et al. |
| 6,056,765 A | 5/2000 | Bajaj et al. |
| 6,071,294 A | 6/2000 | Simons et al. |
| D428,150 S | 7/2000 | Ruf et al. |
| 6,086,545 A | 7/2000 | Roe et al. |
| 6,136,013 A | 10/2000 | Marshall et al. |
| 6,152,942 A | 11/2000 | Brenneman et al. |
| 6,156,050 A | 12/2000 | Davis et al. |
| 6,156,051 A | 12/2000 | Schraga |
| 6,168,606 B1 | 1/2001 | Levin et al. |
| 6,183,489 B1 | 2/2001 | Douglas et al. |
| 6,190,398 B1 | 2/2001 | Schraga |
| 6,192,891 B1 | 2/2001 | Gravel et al. |
| 6,197,040 B1 | 3/2001 | LeVaughn et al. |
| 6,210,420 B1 | 4/2001 | Mauze et al. |
| 6,221,089 B1 | 4/2001 | Mawhirt |
| 6,228,100 B1 | 5/2001 | Schraga |
| 6,258,112 B1 | 7/2001 | Schraga |
| 6,283,982 B1 | 9/2001 | Levaughn et al. |
| 6,306,152 B1 | 10/2001 | Verdonk et al. |
| 6,322,574 B1 | 11/2001 | Lloyd et al. |
| 6,322,575 B1 | 11/2001 | Schraga |
| 6,332,871 B1 | 12/2001 | Douglas et al. |
| 6,346,114 B1 | 2/2002 | Schraga |
| 6,358,265 B1 | 3/2002 | Thorne, Jr. et al. |
| 6,364,889 B1 | 4/2002 | Kheiri et al. |
| 6,379,317 B1 | 4/2002 | Kintzig et al. |
| 6,395,495 B1 | 5/2002 | Montagnier et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,464,649 B1 | 10/2002 | Duchon et al. |
| 6,506,168 B1 | 1/2003 | Fathallah et al. |
| 6,514,270 B1 | 2/2003 | Schraga |
| 6,540,762 B1 | 4/2003 | Bertling |
| 6,558,402 B1 | 5/2003 | Chelak et al. |
| 7,087,068 B1 | 8/2006 | Marshall et al. |
| 7,175,641 B1 | 2/2007 | Schraga |
| 7,311,718 B2 | 12/2007 | Schraga |
| 2001/0027327 A1 | 10/2001 | Schraga |
| 2001/0039387 A1 | 11/2001 | Rutynowski et al. |
| 2002/0077650 A1 | 6/2002 | Schraga |
| 2003/0050655 A1 | 3/2003 | Roe |
| 2003/0050656 A1 | 3/2003 | Schraga |
| 2005/0234495 A1 | 10/2005 | Schraga |
| 2006/0173478 A1 | 8/2006 | Schraga |
| 2006/0241668 A1 | 10/2006 | Schraga |
| 2008/0033468 A1 | 2/2008 | Lathrop et al. |
| 2008/0039885 A1 | 2/2008 | Purcell |

FOREIGN PATENT DOCUMENTS

| | | |
|---|---|---|
| EP | 0061102 | 9/1982 |
| EP | 0137975 | 4/1985 |
| EP | 0189117 | 7/1986 |
| EP | 0 838 195 | 4/1998 |
| EP | 0885590 | 12/1998 |
| EP | 0904731 | 3/1999 |
| EP | 1074219 | 2/2001 |
| EP | 1 142 534 | 7/2004 |
| EP | 0 885 590 | 1/2008 |
| FR | 1126718 | 11/1956 |
| KR | 10-2001-0020623 | 3/2003 |
| WO | WO 93/19671 | 10/1993 |
| WO | 99/63897 | 12/1999 |
| WO | 03/022130 | 3/2003 |

* cited by examiner

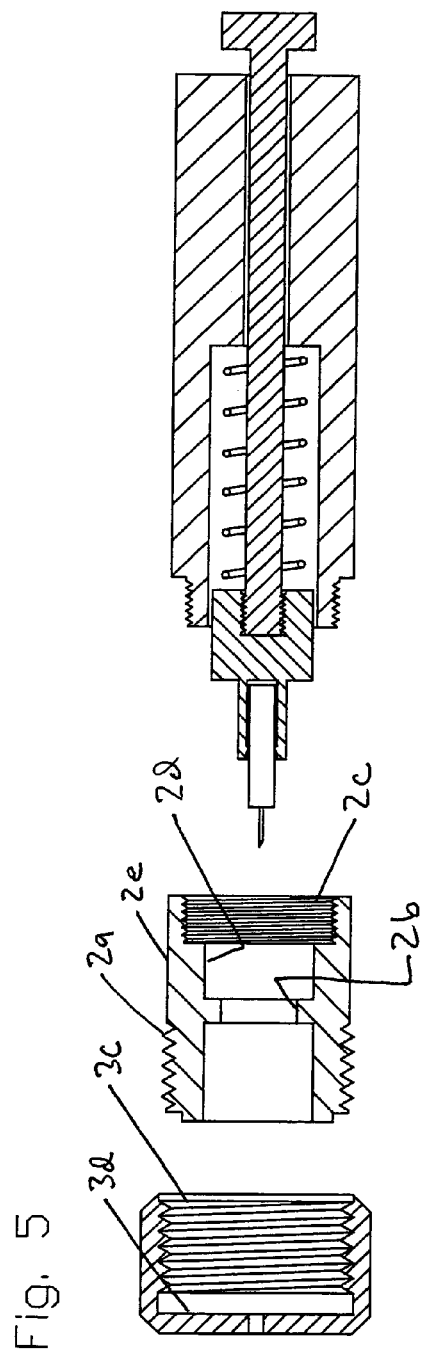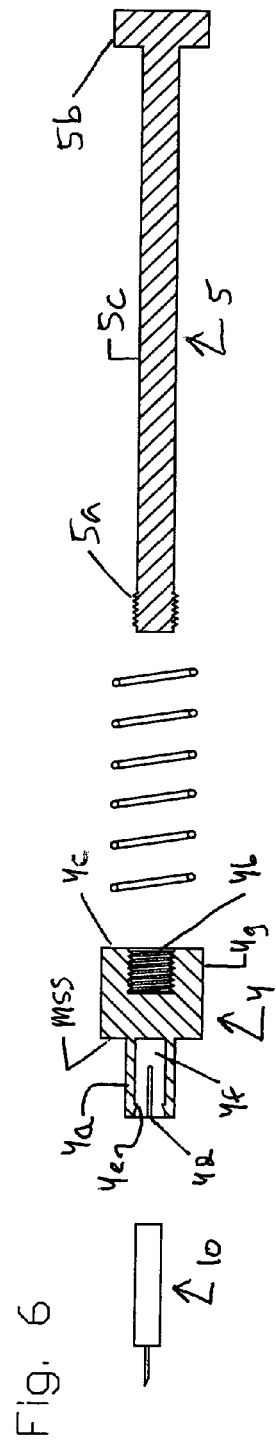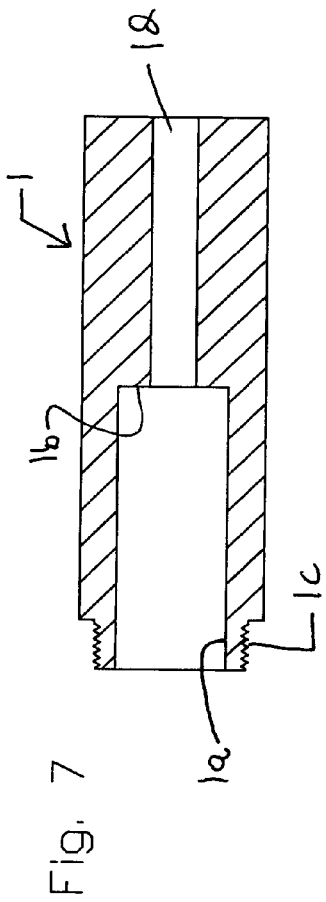

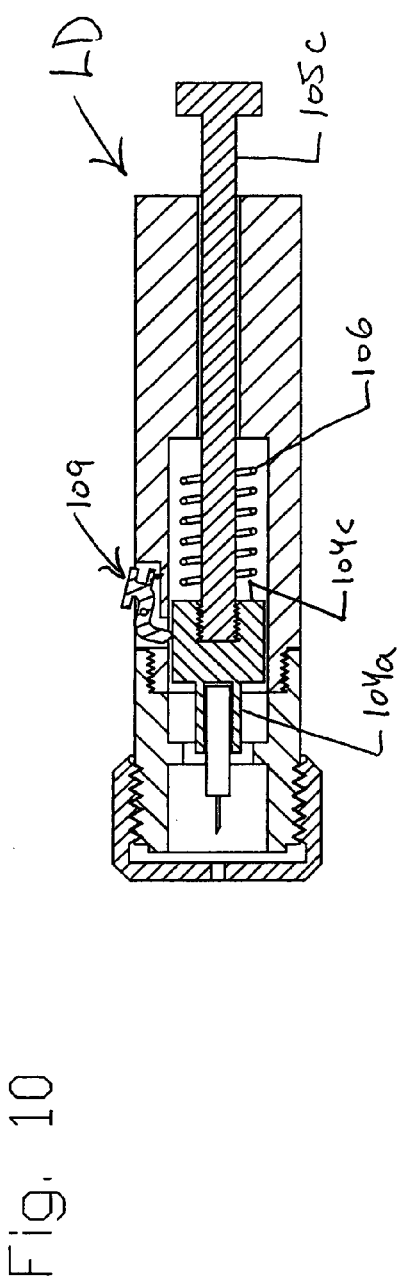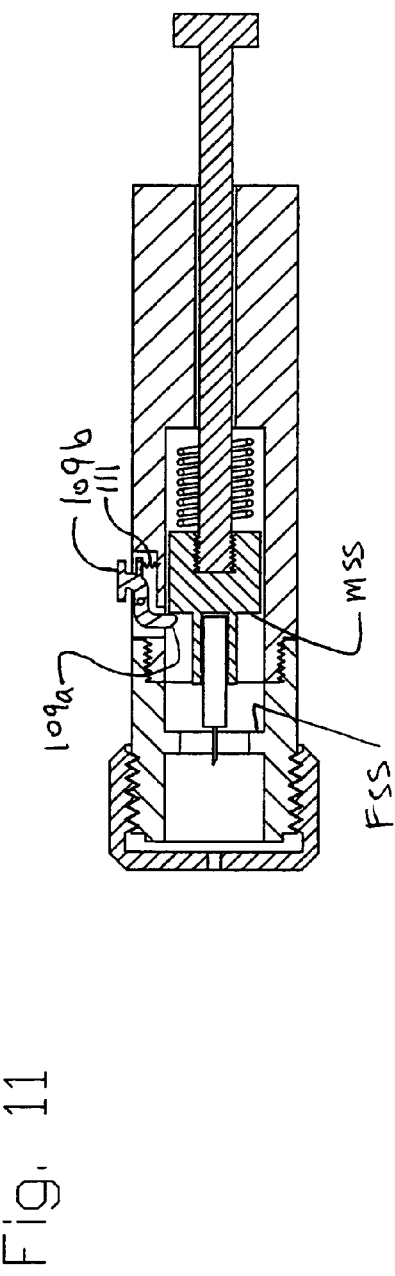
Fig. 10
Fig. 11

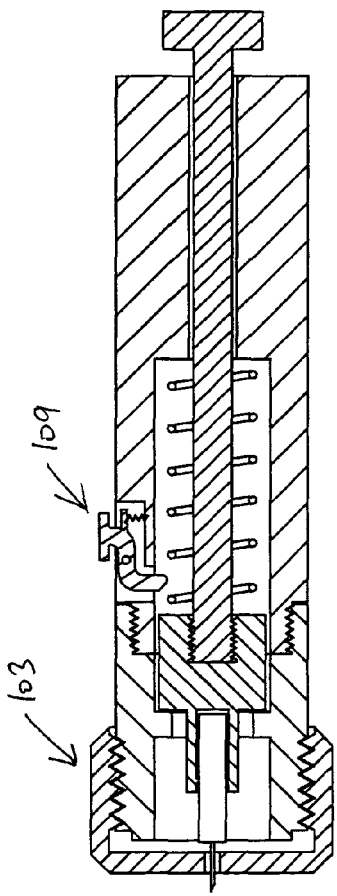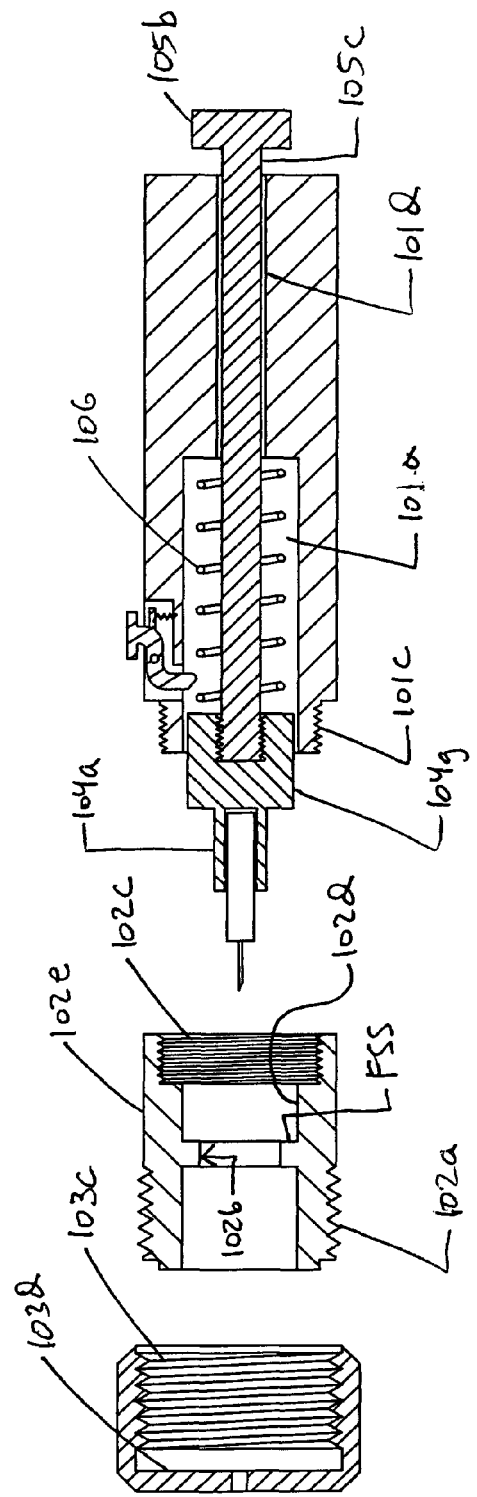
Fig. 12
Fig. 13

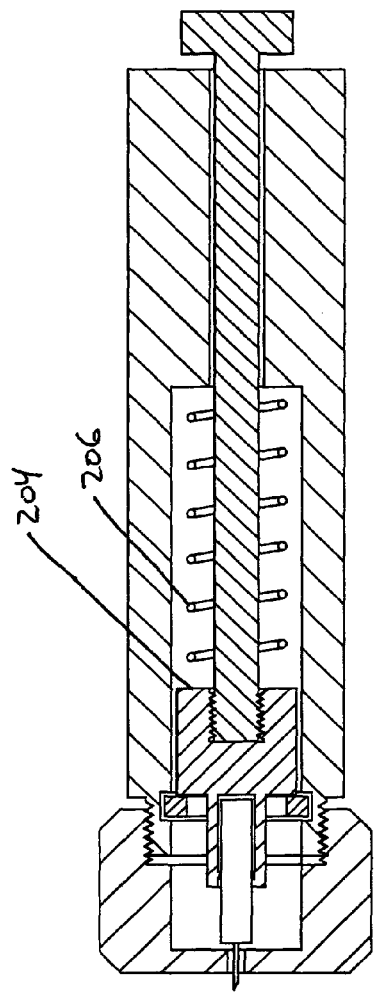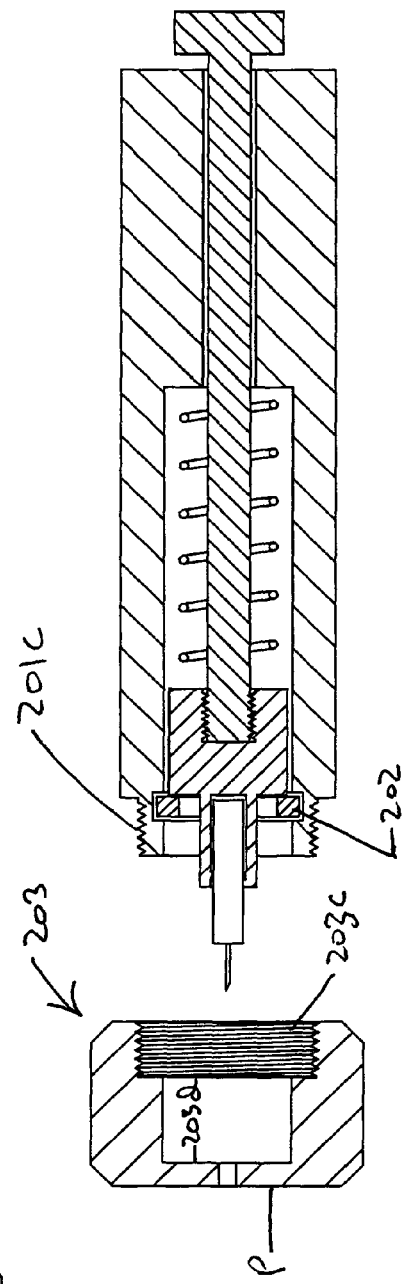
Fig. 18
Fig. 19

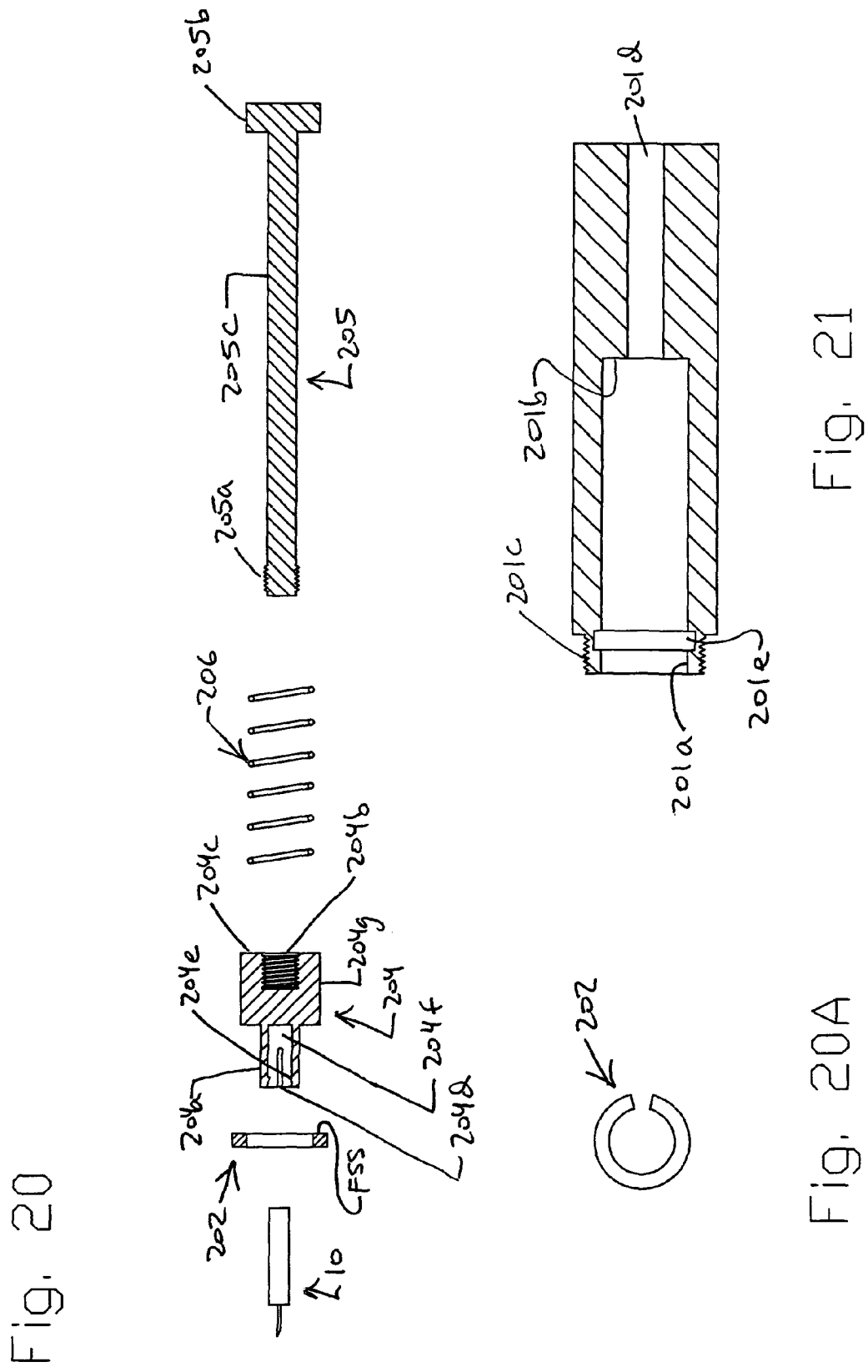

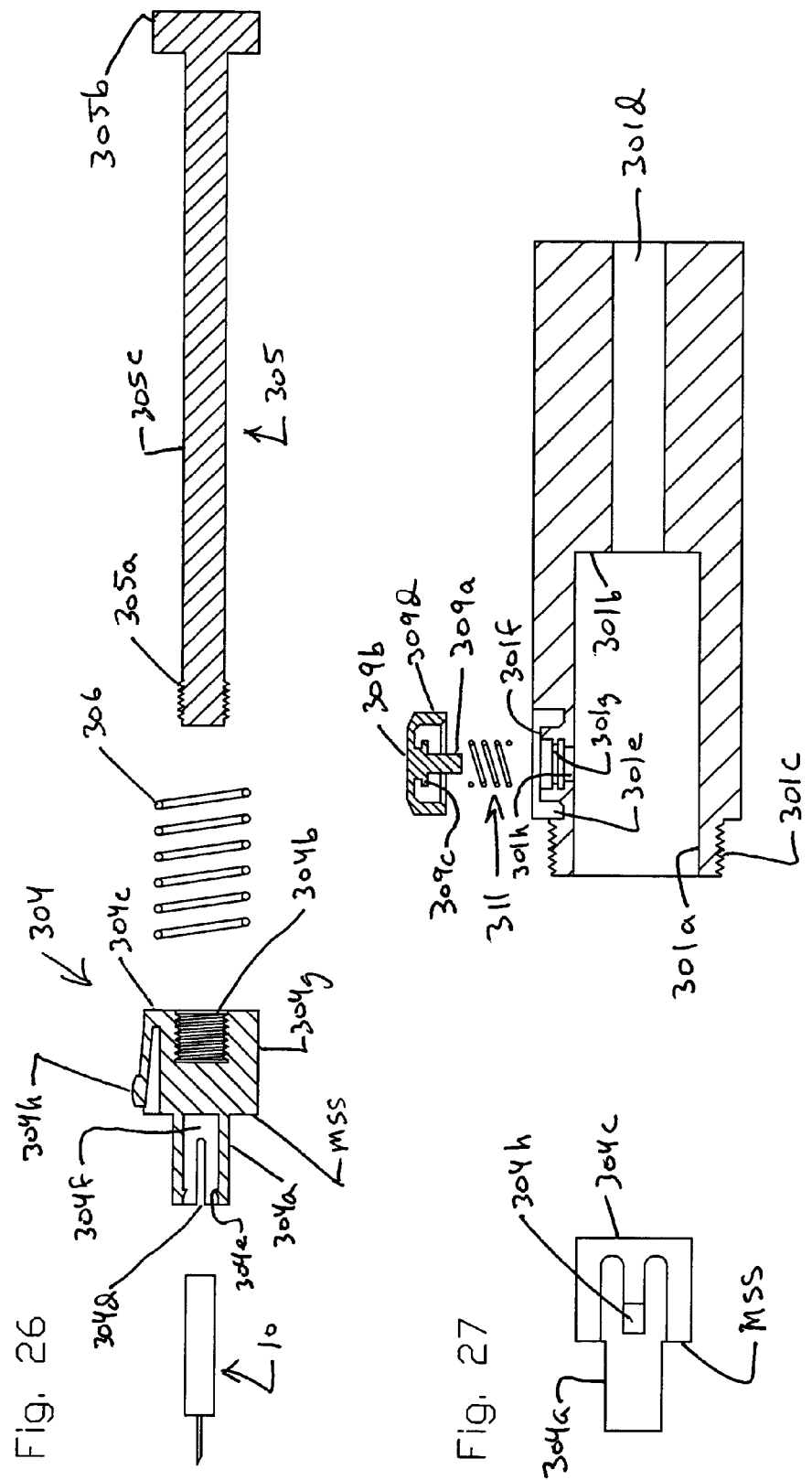

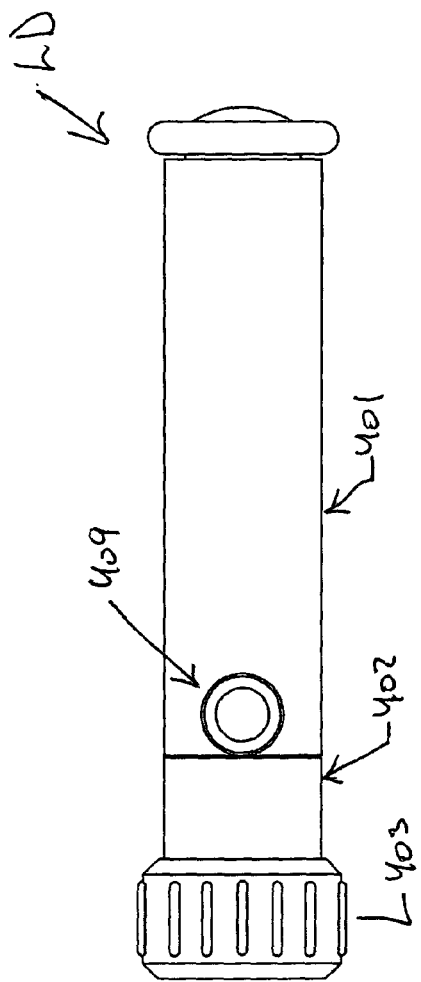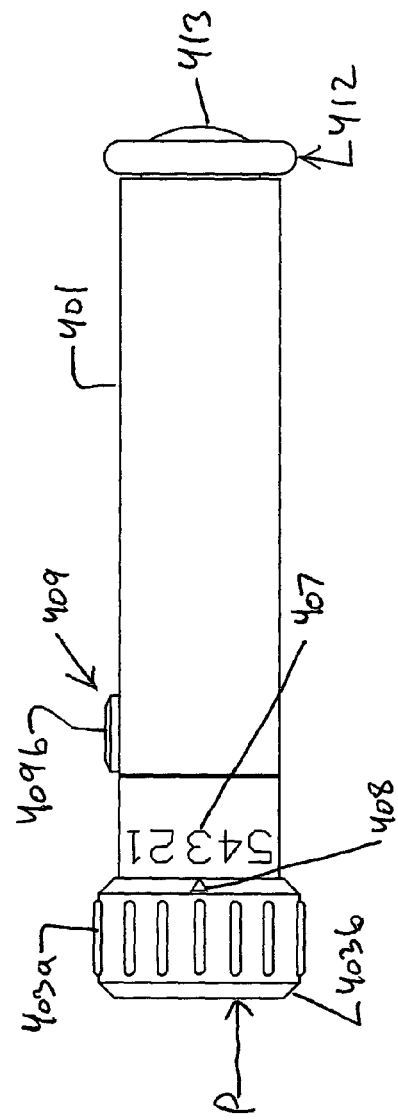
Fig. 29
Fig. 30

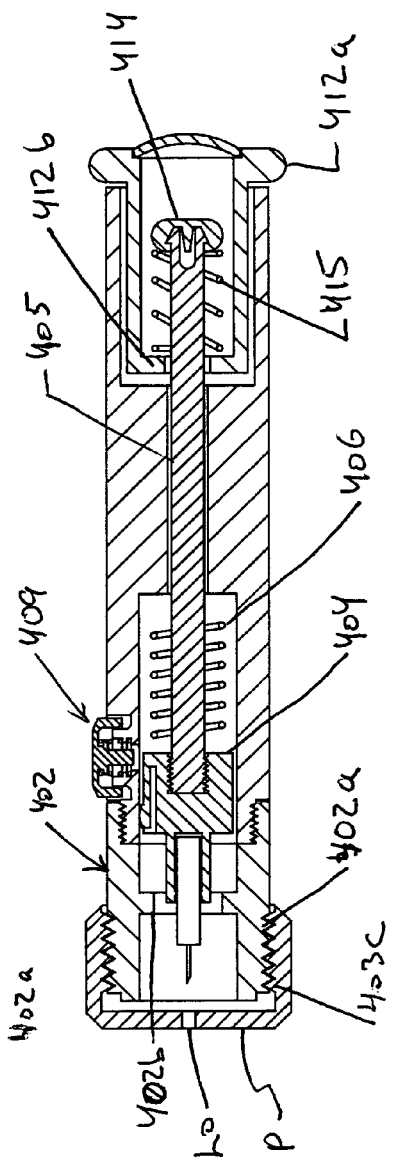
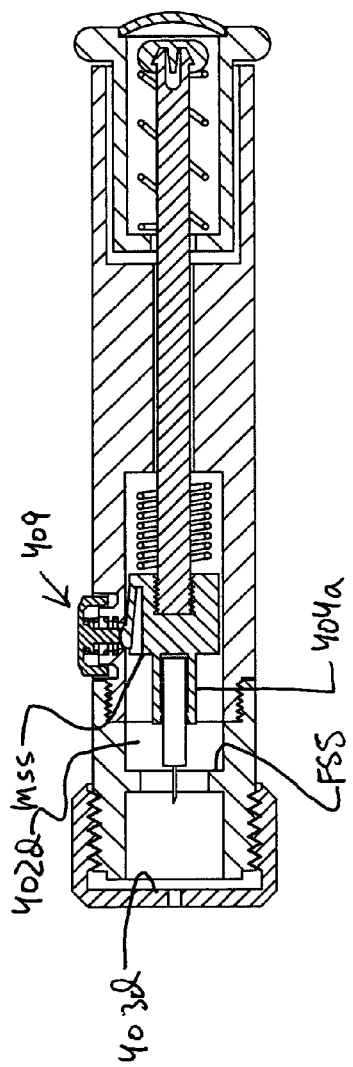
Fig. 31
Fig. 32

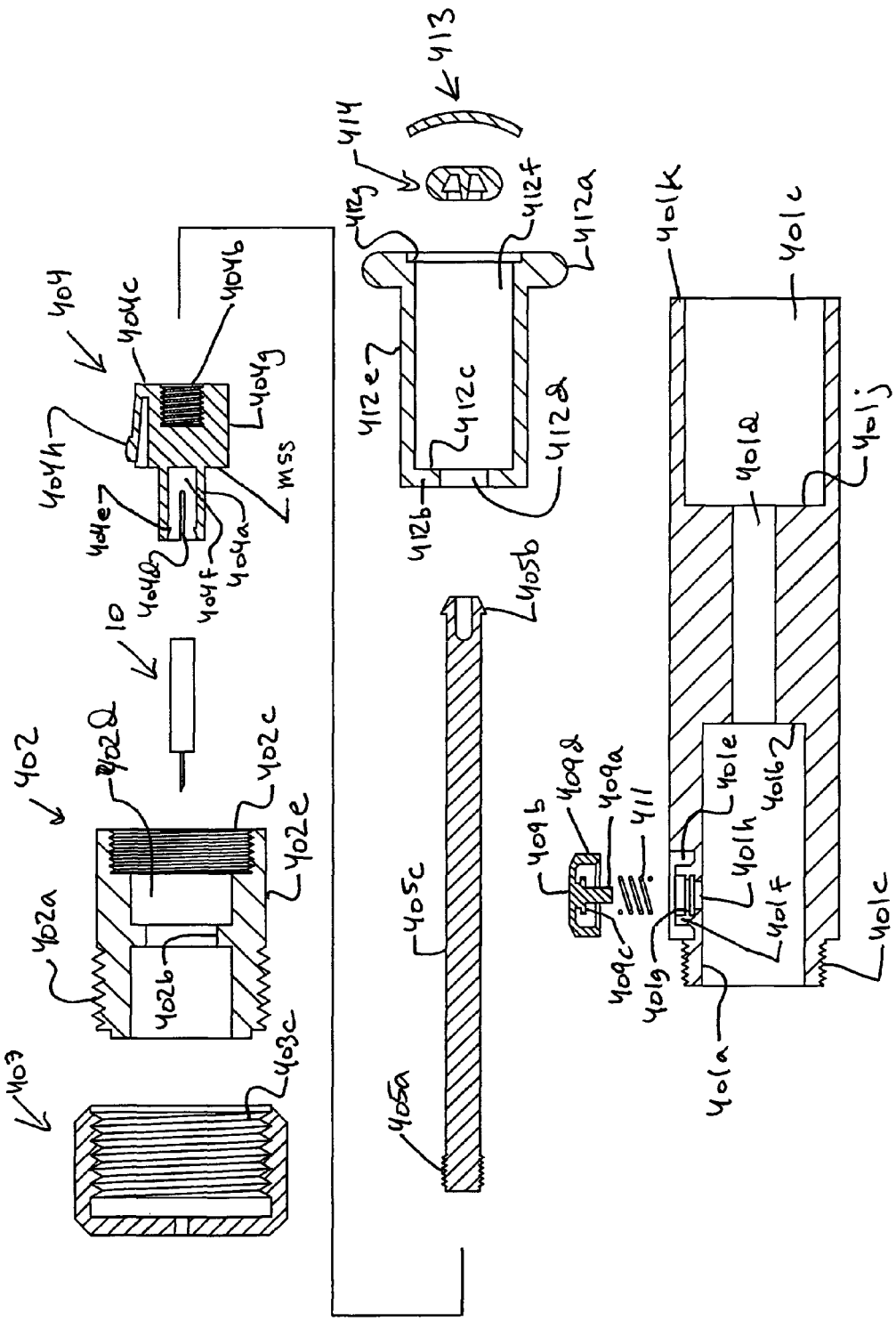

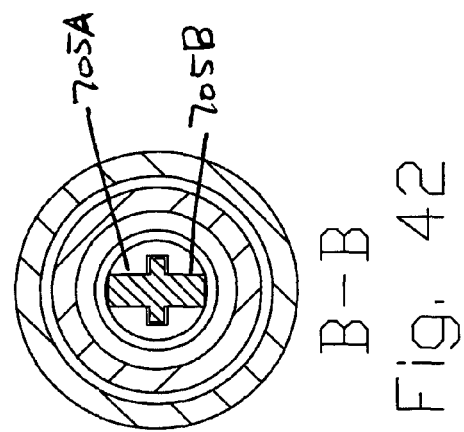
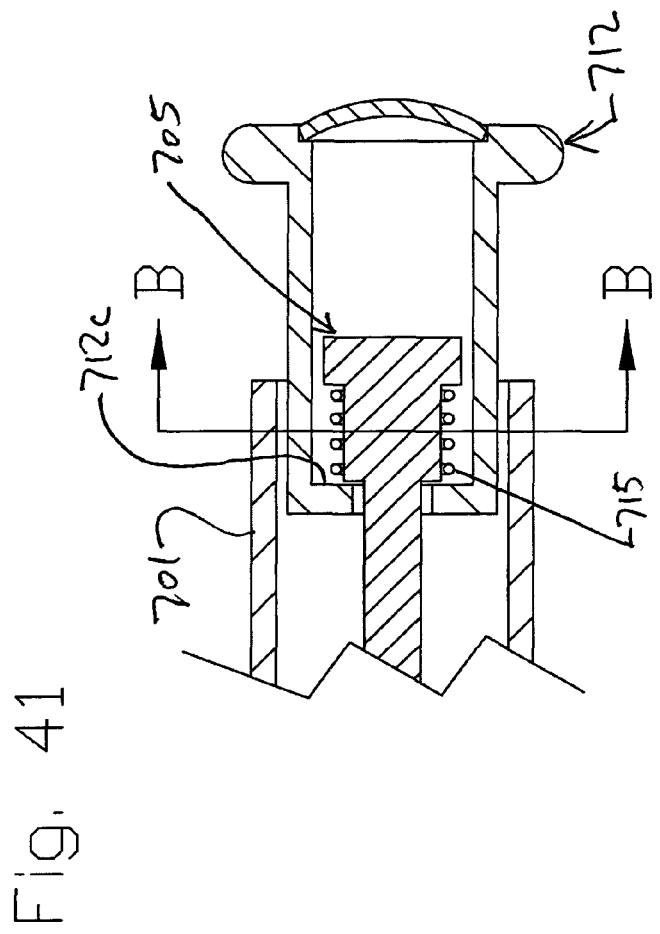
Fig. 41
Fig. 42  B-B

C-C

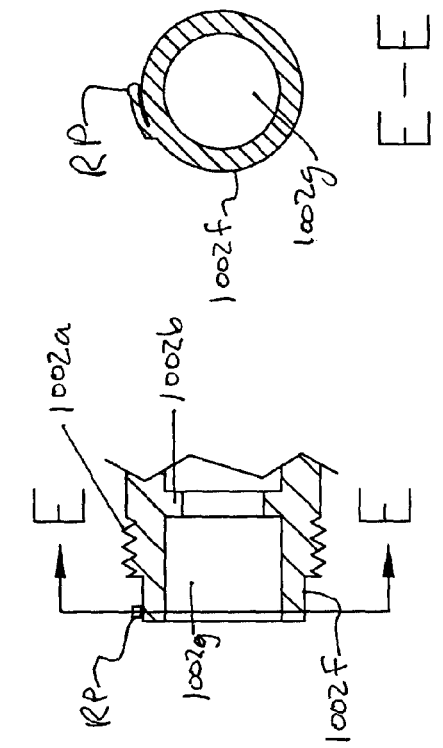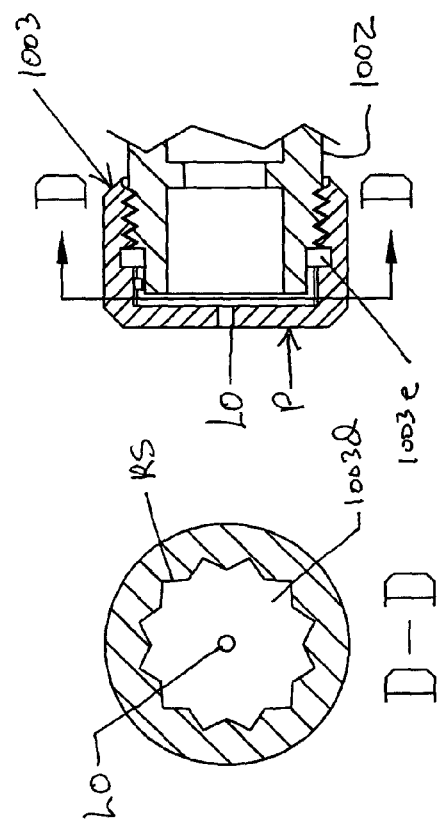
Fig. 50
Fig. 49
Fig. 48
Fig. 47

ADJUSTABLE LANCET DEVICE AND METHOD

BACKGROUND OF THE INVENTION

1. Field of the Invention

The invention relates to a lancet device which is easier, more economical and which is more efficient to make. The invention also relates to a lancet device preferably having an adjusting capability, and a method of using a lancet device. In particular, the invention relates to a lancet device which utilizes an adjustable depth penetration. Lancet devices are used to penetrate and puncture the skin in order to allow the taking of a blood sample for testing. The present device allows the user to control the depth of this penetration by a simple adjustment mechanism.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more callused than a middle finger, and the more callused finger will typically have thicker skin. By adjusting the depth of puncture so that the depth is no greater than necessary for extracting a required amount of blood, any pain experienced by the user may be minimized.

Lancets having an adjustable tip are known per se. For example, U.S. Pat. No. 4,469,110 to SLAMA discloses a mechanism which adjusts the penetration depth by rotating a threaded sleeve relative to a body. The SLAMA device is characterized as a "single bottom" device which employs a threaded design which can be expensive to manufacture. Moreover, such a device may require the user to rotate the threaded sleeve up to 360 degrees and more in order to attain the proper depth setting. Further, such a threaded resign is prone to inadvertent setting changes since there is nothing but frictional engagement between the mating threads to maintain the adjustment setting.

U.S. Pat. No. 4,895,147 to BODICKY et al. functions in a similar manner to the device in SLAMA and therefore suffers from similar disadvantages.

U.S. Pat. Nos. 5,464,418, 5,797,942, 5,908,434, 6,156,051 and 6,530,937 to SCHRAGA also disclose similar lancet devices and are hereby incorporated herein by reference as though set forth in full herein.

As disclosed in U.S. Pat. No. 5,908,434, the lancet device has a body portion which encloses a lancet and a lancet firing mechanism. The lancet typically has a needle extending therefrom and is caused to move towards the tip of the device by a trigger or firing mechanism. The lancet device forces the needle, by virtue of the needle being fixed thereto, out of the device by some distance or depth so that the needle can penetrate the skin of the user. The function of this firing mechanism and the lancet body design is disclosed in each of U.S. Pat. Nos. 5,797,942 and 5,908,434. These Patents are incorporated by reference herein in their entirety and are therefore only briefly discussed herein. Similarly, U.S. Pat. No. 6,156,051 discloses a lancet device which utilizes a lancet firing mechanism, a depth adjustment mechanism, and a trigger setting mechanism. This patent is incorporated by reference herein in its entirety.

What is needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices.

Thus, while advances have been made, there is a continuing need for a lancet device which provides for convenient, reliable and easy adjustment of penetration depth.

SUMMARY OF THE INVENTION

According to one aspect of the invention there is provided a lancet device that includes a body. A trigger is mounted to the body. A front cover includes a skin engaging end that includes a lancet opening through which a lancet needle extends. A holding member is movably mounted within the body and comprises a front end and a rear end. The front end is configured to receive a lancet. A movable stop surface moves with the holding member. The front cover can move axially to adjust the depth of penetration of the lancet needle. A fixed stop surface is arranged within the body. The movable stop surface preferably contacts the fixed stop surface at every depth setting.

The lancet device may further comprise a back cap configured to move between a retracted position and an original position. The back cap may be configured to move the holding member to a retracted position. The back cap may be coupled to a surface that engages the rear end of the holding member. The back cap may include a surface that engages the rear end of the holding member. The back cap may comprise an opening that receives a rear end of the holding member. The back cap may include a surface that engages projections disposed on the rear end of the holding member.

The lancet device may further comprise a spring for biasing the back cap towards an original position. The lancet device may further comprise a first spring for biasing the holding member towards an extended position and a second spring for biasing the holding member in an opposite direction. The first and second springs may be arranged within an axial opening of the body. The first spring may contact one side of a projection extending inwardly from the body and the second spring may contact another side of the projection. The projection may have portions that extend into a recess or indentation formed in the holding member.

The lancet device may further comprise an end plug mounted to the rear end of the holding member. The first spring may be disposed between a projection wall and an inner wall surface arranged in the area of the front end of the holding member and the second spring may be disposed between a projection wall and the end plug. The trigger may be movably mounted to the body. The front cover may be removably mounted to the body. The holding member may be integrally formed with the stop surface. The front end of the holding member may comprise an opening that is configured to removably receive the lancet.

The lancet device may further comprise a deflecting member configured to be deflected by the trigger. The deflecting member may be coupled to the holding member. The deflecting member may comprise a first stop surface or end that contacts a first surface of a holding surface of the body. The front cover may comprise indicia. The front cover may include external protrusions and/or a textured gripping surface. The front cover may include internal threads while an outer circumferential surface of the front cover includes the indicia. An intermediate section may be disposed between the front cover and the body. The intermediate section may have an opening which is large enough to allow the holding member to move within it. The opening may comprise a center axis that is generally the same as the axis running through the holding member. The front cover may rotate about an axis that is generally substantially the same as an axis running through at least one of the lancet opening and the holding member. The fixed stop surface may be disposed between the trigger and a front cover. The body may comprise a two piece body. The lancet device may further include a mechanism for maintaining a depth set position of the front cover. The fixed stop surface may be disposed between the movable stop surface and an inside annular surface of the front cover. The front cover may be removably mounted to the two piece body. The lancet device may further comprise a back cap movably mounted to the two piece body. The body may comprise an ergonomic shape which is easy to grip. The body may comprise indicia.

The invention also provides a method of puncturing a surface of skin using the lancet device described above, wherein the method comprises adjusting a set depth of penetration of the needle by moving the front cover to a desired set position, disposing the skin engaging end of the lancet device against a user's skin, and triggering the trigger to cause the lancet needle to penetrate the user's skin, wherein the puncture allows a blood sample to be taken.

The invention also provides a method of using the lancet device described above, wherein the method comprises at least partially rotating the front cover to a desired set position, moving the holding member to a retracted position, maintaining the holding member in the retracted position until the trigger is triggered, disposing the skin engaging end of the lancet device against a user's skin, and triggering the trigger to cause movement of the holding member.

The invention also provides a lancet device, that preferably includes a body, a trigger, a front cover comprising a skin engaging end that includes a lancet opening through which a lancet needle extends. A holding member may be movably mounted within the body and comprising a front end a rear end. The front end is configured to receive a lancet. A stop surface may be coupled to the holding member. The front cover comprises indicia. A fixed stop surface is preferably arranged to contacted by the movable stop surface. The front cover is preferably configured to rotate at least partially.

The invention also provides a lancet device preferably comprising a body, a trigger, a front cover comprising a skin engaging end that includes a lancet opening through which a lancet needle extends. A holding member may be movably mounted within the body and comprising a front end a rear end. The front end is configured to receive a lancet. A back cap may be configured to move the holding member to a retracted position. A stop surface may be coupled to the holding member. The front cover preferably comprises indicia. A fixed stop surface may be coupled to the body and can be contacted by the stop surface. The front cover may be configured to rotate at least partially on an axis that is parallel to an axis of the holding member.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 5 shows a side cross-section view of the embodiment shown in FIG. 1. The device is shown in a partially disassembled state with the front cover and intermediate section being separated from the body;

FIG. 6 shows a side cross-section view of the internal parts of the embodiment shown in FIG. 1. The parts are shown in a disassembled state with the lancet, front lancet holder, spring and rear lancet holder being separated from each other;

FIG. 7 shows a side cross-section view of the body used in the embodiment shown in FIG. 1;

FIG. 10 shows a side cross-section view of the embodiment of FIGS. 8 and 9. The device is shown with the lancet needle in an intermediate position prior to being pulled back and released. The lancet is not shown in cross-section;

FIG. 11 shows a side cross-section view of the embodiment shown in FIG. 10. The device is shown with the lancet needle pulled back to a retracted position;

FIG. 12 shows an enlarged side cross-section view of the embodiment shown in FIG. 10 with the lancet needle in the fully extended puncturing position;

FIG. 13 shows a side cross-section view of the embodiment shown in FIG. 12. The device is shown in a partially disassembled state with the front cover and intermediate section being separated from the body;

FIG. 18 shows an enlarged side cross-section view of the embodiment shown in FIG. 14 with the lancet needle in the fully extended puncturing position. The protective cover is not shown;

FIG. 19 shows a side cross-section view of the embodiment shown in FIG. 18. The device is shown in a partially disassembled state with the front cover being separated from the body;

FIG. 20 shows a side cross-section view of the internal parts of the embodiment shown in FIG. 14. The parts are shown in a disassembled state with the lancet, snap ring, front lancet holder, spring and rear lancet holder being separated from each other;

FIG. 20A shows a front view of the snap ring used in the embodiment shown in FIG. 14;

FIG. 21 shows a side cross-section view of the body used in the embodiment shown in FIG. 14;

FIG. 26 shows an enlarged side cross-section view of the internal parts of the embodiment shown in FIG. 22. The parts are shown in a disassembled state with the lancet, front lancet holder, spring and rear lancet holder being separated from each other;

FIG. 27 shows a enlarged top view of the front lancet holder used in the embodiment shown in FIG. 22;

FIG. 28 shows an enlarged side cross-section view of the body used in the embodiment shown in FIG. 22. The trigger and trigger spring are shown disassembled from the body;

FIG. 29 shows a top view of another embodiment of the lancet device. This embodiment utilizes a push-button trigger and a trigger setting or arming mechanism;

FIG. 30 shows a side view of the embodiment shown in FIG. 29;

FIG. 31 shows a side cross-section view of the embodiment of FIG. 29. The device is shown with the lancet needle in an intermediate position prior to being pulled back and released. The lancet is not shown in cross-section;

FIG. 32 shows a side cross-section view of the embodiment shown in FIG. 29. The device is shown with the lancet needle pulled back to a retracted position;

FIG. 34 shows an enlarged side cross-section view of certain parts of the embodiment shown in FIG. 29. The parts are shown in a disassembled state with the front cover, intermediate section, lancet, front lancet holder, rear lancet holder, spring retainer, and end plug being separated from each other. The front and back springs and the body are not shown;

FIG. 35 shows an enlarged side cross-section view of the body used in the embodiment shown in FIG. 29. The trigger and trigger spring are shown disassembled from the body;

FIG. 41 shows a partial enlarged side cross-section view of another embodiment. This embodiment is similar to that shown in FIG. 36, except that the rear holding member uses rear projections to support the rear spring and which are engaged by the back cap when the back cap is pulled back to the extended or arming position;

FIG. 42 shows a section view of the arrows B-B shown in FIG. 41. The cross-shaped opening and the cross-shaped cross-section of rear portion of the holding member is shown, as are the two rear projections;

FIG. 47 shows a rear cross-section view of the front cap shown in FIG. 48. The section view illustrates one possible configuration of the internal ratchet surface;

FIG. 48 shows a partial side cross-section view of one possible system for maintaining the depth setting of the front cap;

FIG. 49 shows a partial side cross-section view of the intermediate section shown in FIG. 48; and FIG. 50 shows a rear cross-section view of the front end of the intermediate section shown in FIG. 48.

DETAILED DESCRIPTION OF THE PRESENT INVENTION

Figure 1:
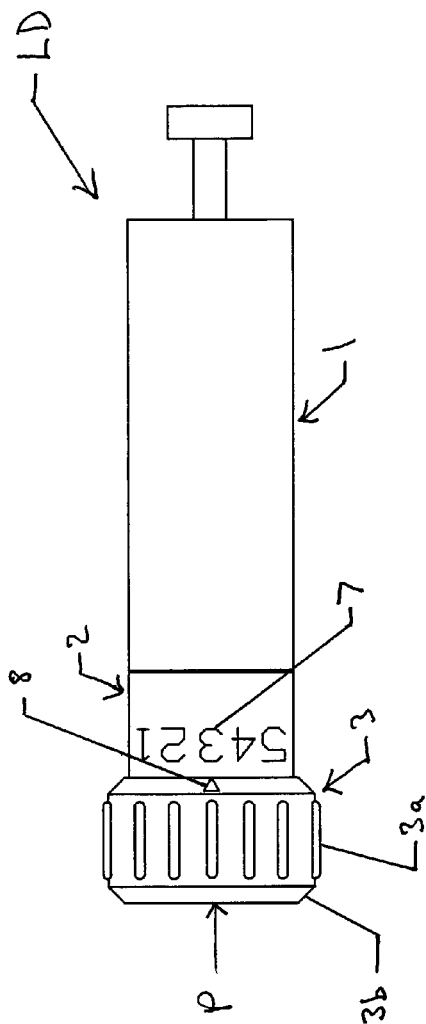
FIG. 1 shows a side view of one embodiment of the lancet device. The device is shown in an intermediate depth setting position.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-7 show various views of one embodiment of lancet device. Lancet device LD has three main external parts, i.e., a lancet body 1, an intermediate section 2, and a front cover or cap 3. These parts 1, 2 and 3 are connected to each other via threads and/or a threaded connection when the lancet device LD is initially assembled. A holding member 4/5 is movably disposed within the body 1. The front cover or cap 3 is removably connected or attached to a front portion of the body 1. By removing the front cover 3, and optionally the intermediate section 2, one can gain access to the lancet 10. The lancet 10 can thus be removed and replaced with a new lancet 10, as needed, once the front cover 3 and intermediate section 2 are removed. As in many lancet devices, the lancet device defines a plane P which is configured to contact (i.e., be positioned against) a user's skin. Although not shown, the instant embodiment may utilize, e.g., a planar, an inwardly curved surface plane, or an outwardly curved plane P beyond which the lancet need can extend. The plane P is arranged on the front cap 3. The lancet holder 4/5 has a front portion 4 and a rear portion 5 which includes a gripping portion 5b that can be gripped by a user. The front portion 4 and the rear portion 5 are connected to each other and are able to slide within the body 1. Of course, the invention also contemplates that the front portion 4 and rear portion 5 can be formed as a one piece member. As will be described in more detail later on, movement of the gripping portion 5b rearwardly (see FIG. 3), causes the holding member 4/5 to retract until it reaches a spring loaded position shown in FIG. 3. The lancet 10, itself, is conventional and includes a needle. It can be removed and replaced with a new one, as is the case in many lancet devices. To ensure that lancet 10 is securely (yet removably) retained within the lancet device LD, the front portion 4 of the holding member 4/5 includes a lancet holding end 4a which receives the lancet 10 therein.

Figure 2:
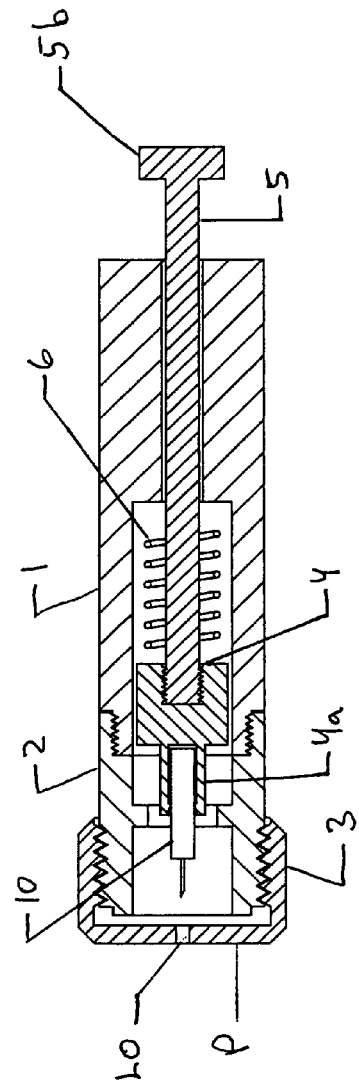
FIG. 2 shows a side cross-section view of the embodiment of FIG. 1. The device is shown with the lancet needle in an intermediate position prior to being pulled back and released. The lancet is not shown in cross-section.

As can be seen in FIG. 2, the holding member 4/5 arrangement preferably has a main spring 6 mounted thereto. In this regard, the spring 6, which can be made of spring steel, is arranged to surround the holding member 4/5 in an area of the rear portion 5. Accordingly to one non-limiting example, the spring 6 has a diameter of approximately 6.2 mm, a freelength of approximately 36.7 mm, and a wire size of 0.5 mm. Of course, other sizes and types of springs can be used provided they function for their intended purpose. Other materials (e.g., metal, plastic or composite) for the spring are also contemplated. This spring 6 causes (and/or biases) the holding member 4/5 to move towards an extended position once the holding member 4/5 is pulled back (see FIG. 3). When a user wishes to place the lancet device LD in the loaded position, a user need only move gripping portion 5b rearwardly (see FIG. 3) until the holding member arrangement 4/5 reaches the position shown in FIG. 3. This, in turn, compresses the spring 6 to a certain extent. However, when the user releases the gripping portion 5b, spring 6 automatically causes the holding member 4/5 to move to a fully extended position shown in FIG. 4. However, once contact occurs between stop surface MSS and stop surface FSS (compare FIGS. 3 and 4), the spring 6 causes the holding member 4/5 to automatically retract axially back into the body 1 to a position similar to that of FIG. 2. Although not shown, this occurs because the spring 6 has one end, i.e., the left end, coupled to the front portion 4 of the holding member 4/5 and another end, i.e., the right end, coupled to the annular surface 1b of the body 1. One way this can occur is shown in FIG. 46, which will be more fully described later on. The spring 6 can, of course, be connected to these parts in any desired manner. Alternatively, the spring 6 can be connected to the front part and body in a manner similar to that of FIG. 45, i.e., via flanges formed on the parts 1 and 4. Using such an arrangement, the lancet needle only momentarily projects past the plane P in the extended position before it is caused to retract back in the lancet device by the spring 6. As a result, the lancet needle only projects past or beyond the plane P for a very brief time (i.e., a fraction of a second when the gripping end 5b is released) and is otherwise not exposed to a user while the front cover 3 is installed thereon. Accordingly, a user or other innocent bystanders can be protected from being injured unintentionally by an exposed needle.

The lancet device LD utilizes the front cap 3 to adjust the penetration depth of the lancet needle. The front cap 3 is preferably mounted to the body 1 and/or to the intermediate section 2 of the body 1 so as to be at least partially rotate in each of two directions. Of course, the front cap 3 can be mounted to the body 2/1 in any desired manner (i.e., with or without threads) provided it functions properly in the intended manner, i.e., provided it moves axially forwards and backwards between discrete set-depth positions. To ensure that the front cap 3 is axially retained to body parts 2 and 1, yet allowed to rotate with respect to the lancet device body 2/1, the front cap 3 has internal threads 3c which engage external threads 2a of the intermediate section 2. The front cap 3 also includes chamfered corners 3b and raised projections 3a which allow a user to more securely grip the front cap 3. The intermediate body section 2 has an internal projecting wall 2b that includes a fixed stop surface FSS (see FIG. 3) which is configured to be engaged by a movable stop surface MSS (in particular stop surface MSS of front portion 4) that is formed on or coupled to the front portion 4 of holding member 4/5.

As described above, FIG. 3 shows the lancet device LD with the lancet member 4/5 in the loaded position, i.e., ready to move to an extended position when the gripping end 5b is released. The holding member 4/5 retains the loaded position of FIG. 3 as long as the user continues to grip the gripping end 5b. On the other hand, FIG. 4 shows what happens when the user releases end 5b. That is, the holding member 4/5 is released from the loaded position of FIG. 3, and is caused to move towards plane P. This occurs because the holding member 4/5 is free to slide within body 1. As will be described later on with regard to other embodiments, the holding member 4/5 can also have a polygonal cross-section shape which corresponds to the polygonal opening 1d in the body 1 so as to ensure that the holding member 4/5 does not substantially rotate while it moves axially back and forth. However, for this embodiment, it is sufficient if the holding member 4/5 has cylindrical outer surfaces (e.g., 4g and 5c) which slide within (with a clearance) cylindrical surfaces (e.g., 2d, 1a and 1d) in the body 1 and intermediate section 2. Again, with regard to FIGS. 3 and 4, it can be seen that the holding member 4/5 can move towards the plane P until the stop surface MSS contacts or engages the stop surface FSS of the intermediate section 2. In this position, the needle of the lancet 10 projects past the plane P and through opening LO and thereby punctures the skin of a user which is resting against the plane P. The lancet device LD is then ready to be reloaded, i.e., it can then be placed back into the position shown in FIG. 3.

FIG. 1 shows the lancet device LD in one of the pre-set extended positions, i.e., in one of the positions of the front cap 3 that will cause a desired puncture depth in the skin of a user (not shown). The distance that the lancet needle projects past plane P is thus determined by rotating the front cap 3 until the desired setting is reached, e.g., arrow 8 lines up with one of the indicia 7. Of course, the invention contemplates that any type of indicia can be used such as, e.g., numbers, letters, symbols, etc. Moreover, the invention also contemplates that the body 1/2 can also contain the arrow while the indicia is placed on the front cap 3. The setting, in turn, causes the plane P to move axially relative to fixed stop surface FSS. Since the movable stop surface MSS always contacts the fixed stop surface FSS in the extended position of the holding member 4/5, since the lancet 10 is secured to the front part 4, and since the plane P moves relative to the fixed stop surface FSS, adjustment of the front cap 3 (by rotation) causes a corresponding change in distance between plane P and the end of the lancet needle, e.g., the rotational position of the front cap 3 thus determines how much of the end of the lancet needle extends past the plane P. The depth setting is thus controlled by contact between the stop surface MSS, stop surface FSS, and the rotational position of the front cap 3. FIG. 4 shows the needle tip projecting through the opening LO in the front cover 3 and past the plane P. Thereafter, the user can pull end 5b back (from the position shown in FIG. 2) to compress spring 6 to again arm the lancet device LD.

Figure 3:
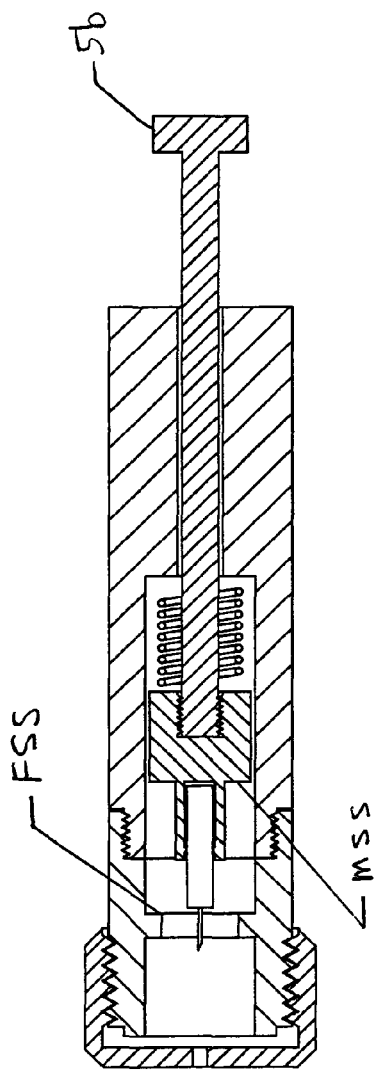
FIG. 3 shows a side cross-section view of the embodiment shown in FIG. 1. The device is shown with the lancet needle pulled back to a retracted position.
Figure 4:
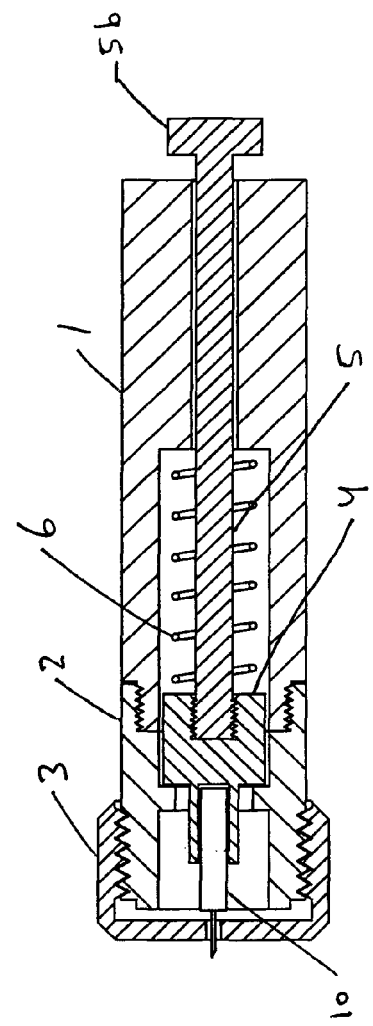
FIG. 4 shows a side cross-section view of the embodiment shown in FIG. 1 with the lancet needle in the fully extended puncturing position.
Figure 8:
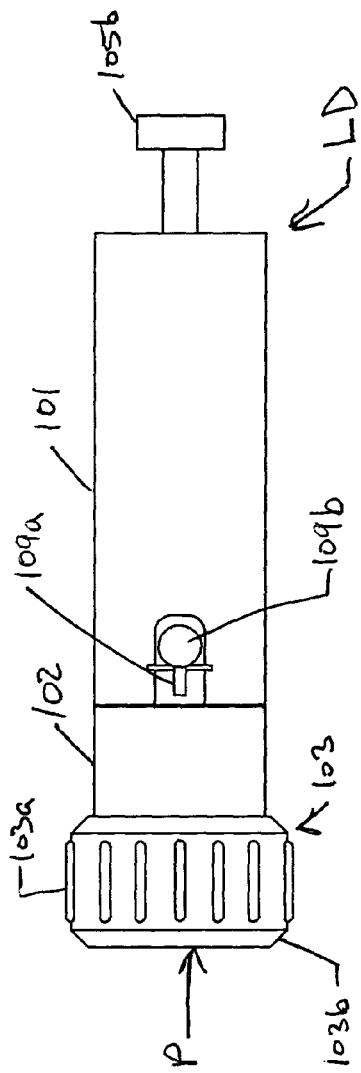
FIG. 8 shows a top view of another embodiment of the lancet device. This embodiment utilizes a trigger mechanism.

FIG. 4 shows a cross-section view of the lancet device of FIGS. 1-3 wherein the holding member 4/5 is in the fully extended position. In this regard, the holding member 4/5 has reached its maximum extended position caused by axial expansion of the spring 6. As in FIGS. 1-3, the front cover 3, intermediate body 2, spring 6, lancet 10 and holding member 4/5 can be seen in their installed and/or assembled position. However, this figure allows one to more clearly see that the spring 6 is arranged to surround the holding member 4/5, just behind the lancet receiving front portion 4. The spring 6 is preferably sized to slide into internal opening 1a of the body 1. More particularly, the spring 6 is preferably disposed inside the body 1 and between an inner wall 1b of the body 1 and surface 4c of the front part 4 of the holding member 4/5. That is, the spring 6 is axially retained between a left side surface 4c of front part 4 of holding member 4/5 the inner wall 1b of the body 1. As a result, the spring 6 is caused to be compressed when the holding member 4/5 is moved back (i.e., to the right) to a retracted position relative to the body 1 and expanded when the holding member 4/5 is moved forward (i.e., to the left) to an extended position relative to the body 1. As discussed above, the spring 6 causes (and/or biases) the holding member 4/5 towards an extended position once a gripping end 5b is released and then back towards a rest position similar to that shown in FIG. 2. As a result, the holding member 4/5 cannot be moved back to a retracted position without causing the spring 6 to be compressed thereby.

As can be seen in FIGS. 5-7, the front cap 3 has internal threads 3c and a planar inner annular surface 3d. Of course, this surface 3d can have any desired configuration since the lancet 10 does not contact the same. The threads 3c are configured to engage external threads 2a of the intermediate section 2. The intermediate section 2 also includes an external cylindrical surface 2e and internal threads 2c which are configured to engage external threads 1c of the body 1. A cylindrical opening 2d is sized to receive (with a clearance) the front portion 4 so that contact can occur between stop surface MSS and stop surface FSS. In this regard, the stop surface FSS is an annular surface that is formed on an internal cylindrical projecting wall 2b which is integral with the section 2. Of course, this wall 2b can instead be formed by spaced projections which extend inwardly from the section 2. Alternatively, this wall 2b can be formed as a separate part and/or removable part (e.g., a snap ring), as in the embodiment shown in FIG. 16. In such case, the intermediate section 2 would include a recess similar to recess 201e in FIG. 21. The front part 4 includes a small cylindrical section 4a which utilizes two oppositely arranged slots 4d. The section 4a also has an internal opening 4f which is sized to receive the rear portion of the lancet 10. In order to ensure that the lancet 10 is securely and axially retained within opening 4f, the front part 4 includes projections 4e which have sharp ends for gripping the lancet 10. These projections can have any desired form provided they securely, yet removably, retain the lancet 10. The slots 4d allow the opening 4f to expand and contract with insertion and removal of the lancet 10 and allow the end 4a to act as two spring fingers. Front part 4 also includes larger cylindrical section 4g which can slide within openings 2d and 1a. In order to connect the front part 4 with the rear part 5 to form the holding member 4/5, the front part 4 includes internal threads 4b which are configured to engage external threads 5a. Of course, these parts can be connected in any desired manner other than threads, e.g., snap connection, adhesives, etc. The rear part 5 also has a cylindrical section 5c which is sized and configured to slide within (with a clearance) cylindrical opening 1d of body 1 and an enlarged cylindrical gripping end 5b.

FIGS. 8-13 show another embodiment of lancet device. Lancet device LD has a lancet body 101 which can be made as a one-piece member as with the embodiment shown in FIGS. 1-7. Alternatively, it can be made as a two-piece structure as in the embodiment shown in, e.g., FIG. 39. Such body parts can, of course, be connected, e.g., using adhesives and/or fasteners and/or welding and/or snap-together holding mechanisms (not shown) to each other when the lancet device LD is initially assembled. A holding member 104/105 is movably disposed within the body 101. Also, a front cover 103 is removably connected or attached to an intermediate section 102 of the body. By removing the front cover 103, one can gain access to the lancet 10. The lancet 10 can thus be removed and replaced with a new lancet 10, as needed, once the front cover 103 is removed. As in the previous embodiment, the lancet device LD defines a plane P which is configured to contact (i.e., be positioned against) a user's skin. Moreover, as with the previous embodiment, the instant embodiment may utilize an inwardly curved and/or an outwardly curved surface plane P beyond which the lancet need can extend. The lancet holder 104/105 has a rear portion 105, and specifically a gripping portion 105b, that can be gripped by a user. The front portion 104 and the rear portion 105 slide within the body 101. As with the previous embodiment, the front part 104 and rear part 105 can alternatively be formed as a one-piece member. As will be described in more detail later on, movement of the gripping portion 105b rearwardly, causes the holding member 104/105 to retract until it reaches a spring loaded position shown in FIG. 11. The lancet 10, itself, is conventional and includes a needle. It can be removed and replaced with a new one, as is the case in many lancet devices. To ensure that lancet 10 is securely (yet removably) retained within the lancet device LD, the front portion 104 of the holding member 104/105 includes a lancet holding end 104a which receives the lancet 10 therein.

As can be seen in FIGS. 10 and 11, the holding member 104/105 arrangement preferably has a spring 106 mounted thereto. In this regard, the spring 106, which can be made of spring steel, is arranged to surround the holding member 104/105, just behind the front portion 104. By way of one non-limiting example, the spring 106 may have a diameter of approximately 6.2 mm, a freelength of approximately 36.7 mm, and a wire size of 0.5 mm. Of course, the spring can be of any desired type, size or material. This spring 106 causes (and/or biases) the holding member 104/105 to move towards an extended position once a trigger 109 is activated (see FIG. 10). The trigger 109 includes a portion 109a that is arranged to extend within the body 1, and is movably and/or pivotally mounted to the body 101. Of course, the trigger 109 can be mounted to the body in any desired manner. The trigger 109 also has a finger engaging (e.g. push button) portion 109b that can be pushed and/or deflected into the lancet device LD. The trigger 109 also utilizes a trigger spring 111 which biases the trigger 109 towards the position shown in FIG. 11. Thus, when force is applied to the finger engaging portion 109b, the inner portion 109a moves away from the front portion 104 and allows it to move towards plane P. On the other hand, when the push button 109b is released, the trigger 109 is capable of returning to the position shown in FIG. 11 or 12.

As discussed above, the spring 106 causes (and/or biases) the holding member 4/5 to move towards an extended position (see FIG. 12) once the holding member 104/105 is pulled back to a loaded or armed (see FIG. 11). When a user wishes to place the lancet device LD in the loaded position, a user need only move gripping portion 105b rearwardly until the holding member arrangement 104/105 reaches the position shown in FIG. 11. This, in turn, compresses the spring 106 to a certain extent. However, when the user presses the trigger 109, end 109a becomes disengaged from front portion 4 and the spring 106 causes the holding member 104/105 to move to a fully extended position. However, once contact occurs between stop surface MSS and stop surface FSS, the spring 106 causes the holding member 104/105 to automatically retract axially back into the body 101 to a position similar to that of FIG. 10. Although not shown, this occurs because the spring 106 has one end, i.e., the left end, coupled to the front portion 104 of the holding member 104/105 and another end, i.e., the right end, coupled to the annular surface 101b of the body 101. One way this can occur is shown in FIG. 46, which will be more fully described later on. The spring 106 can, of course, be connected to these parts in any desired manner. Alternatively, the spring 106 can be connected to these parts 101, 104 in a manner similar to that of FIG. 45, i.e., via flanges formed on the parts 101 and 104. In this way, the lancet needle only momentarily projects past the plane P in the extended position before it is caused to retract back in the lancet device by the spring 106. As a result, the lancet needle only projects past or beyond the plane P for a very brief time (i.e., a fraction of a second when the trigger 109 is released) and is otherwise not exposed to a user while the front cover 103 is installed thereon. Accordingly, a user or other innocent bystanders can be protected from being injured unintentionally by an exposed needle.

As is the case in the previous embodiment, the lancet device LD utilizes the front cap 103 to adjust the penetration depth of the lancet needle. The front cap 103 is preferably mounted to the body 101 and/or to the intermediate section 102 of the body 101 so as to be at least partially rotate in each of two directions. Of course, the front cap 103 can be mounted to the body 101 in any desired manner (i.e., with or without threads) provided it functions properly in the intended manner, i.e., provided it moves axially forwards and backwards. To ensure that the front cap 103 is axially retained to body parts 102 and 103, yet allowed to rotate with respect to the lancet device body, the front cap 103 has internal threads 103c which engage external threads 102a of the intermediate section 102. The front cap 103 also includes chamfered corners 103b and raised projections 103a which allow a user to more securely grip the front cap 103. The intermediate body section 102 has an internal projecting wall 102b that includes a fixed stop surface FSS (see FIG. 11) which is configured to be engaged by a movable stop surface MSS (in particular stop surface MSS of front portion 104) that is formed on or coupled to the front portion 104 of holding member 104/105.

As described above, FIG. 11 shows the lancet device LD with the lancet member 104/105 in the loaded position, i.e., ready to move to an extended position when the trigger 109 is depressed. The holding member 104/105 retains the loaded position of FIG. 11 as long as the user does not press the trigger 109. On the other hand, FIGS. 10 and 12 show what happens when the user presses the trigger 109. That is, the holding member 104/105 is released from the loaded position of FIG. 11, and is caused to move towards plane P. This occurs because the holding member 104/105 is free to slide within body 101. As will be described later on with regard to other embodiments, the holding member 104/105 can also have a polygonal cross-section shape which corresponds to a polygonal opening in the body so as to ensure that the holding member 104/105 does not rotate while it moves axially back and forth. However, for this embodiment, it is sufficient if the holding member 104/105 has cylindrical outer surfaces (e.g., 104g and 105c) which slide within (with a clearance) cylindrical surfaces (e.g., 101a, 102d, and 101d) in the body 101 and intermediate section 102. Again, with regard to FIGS. 10-12, it can be seen that the holding member 104/105 can move towards the plane P until the stop surface MSS contacts or engages the stop surface FSS of the intermediate section 102. In this position, the needle of the lancet 10 projects past the plane P and through opening LO and thereby punctures the skin of a user which is resting against the plane P. The lancet device LD is then ready to be reloaded, i.e., it can then be placed back into the position shown in FIG. 11.

Figure 9:
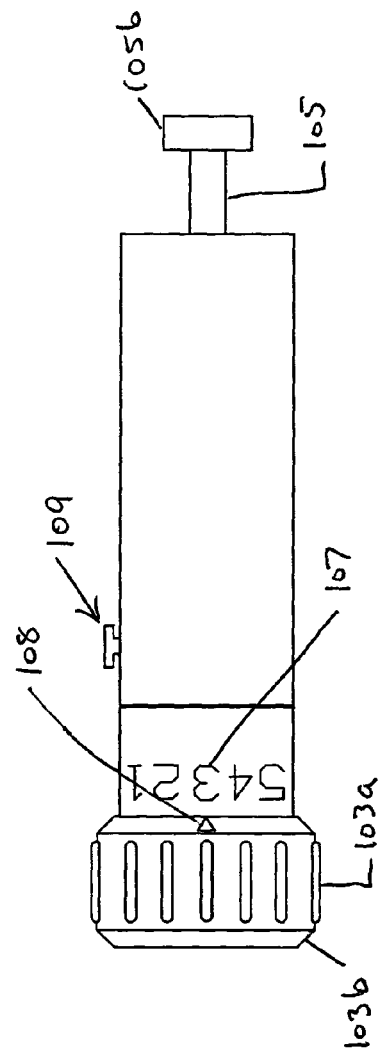
FIG. 9 shows a side view of the embodiment shown in FIG. 8.
Figure 14:
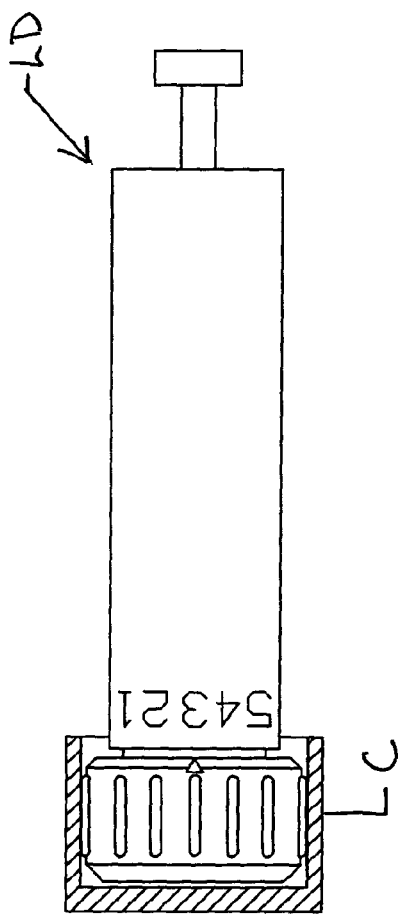
FIG. 14 shows a side view of another embodiment of the lancet device. This embodiment utilizes a protective cover and lacks an intermediate section.
Figure 15:
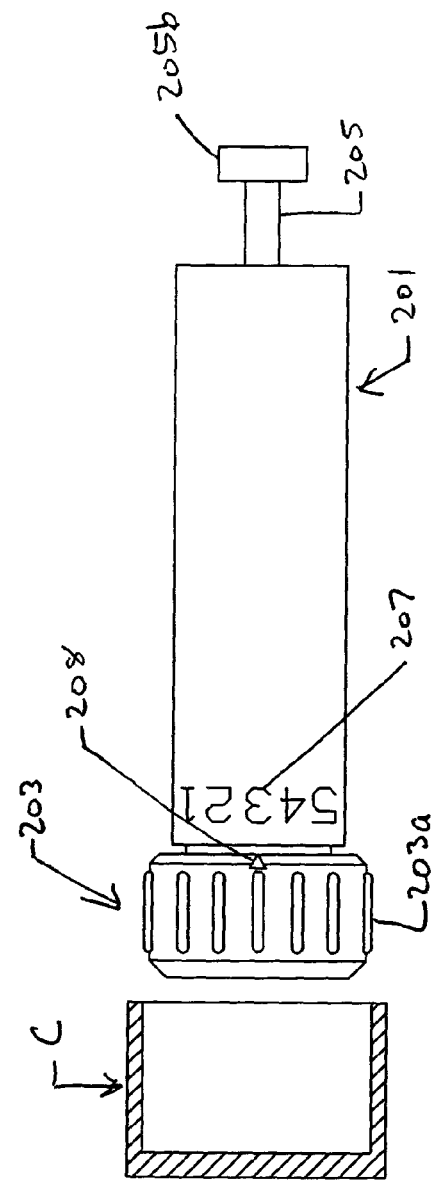
FIG. 15 shows a side view of the embodiment shown in FIG. 14, but with the protective cover being removed.

FIG. 9 shows the lancet device LD in one of the pre-set extended positions, i.e., in one of the positions of the front cap 103 that will cause a desired puncture depth in the skin of a user (not shown). The distance that the lancet needle projects past plane P is thus determined by rotating the front cap 103 until the desired setting is reached, e.g., arrow 108 lines up with one of the indicia 107. Of course, the indicia can be of any type and can be arranged in any desired location of the body 1. Alternatively, the arrow 108 can be arranged on the body 101 while the indicia is arranged on the front cap 103. The setting, in turn, causes the plane P to move axially relative to fixed stop surface FSS, i.e., by rotating the front cap 103 in either of two opposite directions. Since the movable stop surface MSS always contacts the fixed stop surface FSS in the extended position of the holding member 104/105, and since the plane P moves relative to the fixed stop surface FSS, adjustment of the front cap 103 (by rotation) causes a corresponding change in distance between plane P and the end of the lancet needle, e.g., the rotational position of the front cap 103 thus determines how much of the end of the lancet needle extends past the plane P. The depth setting is thus controlled by contact between the stop surface MSS, stop surface FSS and the rotational position of the front cap 103. FIG. 12 shows the needle tip projecting through the opening LO in the front cover 103 and past the plane P. Thereafter, the user can pull end 105b back to compress spring 106 to again arm the lancet device. In this regard, the engaging portion 109a of trigger 109 utilizes an inclined surface which, when engaged by the front portion 104 as it is moved back, causes the trigger 109 to move (against the biasing force of the trigger spring) to the position shown in FIG. 10. Of course, further movement of the front portion 104 backwards will result in the engaging portion falling back (i.e., under the action of the trigger spring) into the setting position shown in FIG. 11.

FIG. 12 shows a cross-section view of the lancet device of FIGS. 8-11 wherein the holding member 104/105 is in the fully extended position. In this regard, the holding member 104/105 has reached its maximum extended position caused by axial expansion of the spring 106. As in FIGS. 8-11, the front cover 103, intermediate body 102, spring 106, lancet 10 and holding member 104/105 can be seen in their installed and/or assembled position. However, this figure allows one to more clearly see that the spring 106 is arranged to surround the holding member 104/105, just behind the lancet receiving front portion 104. The spring 106 is preferably sized to slide into internal opening 101a of the body 101. More particularly, the spring 106 is preferably disposed inside the body 101 and between an inner wall 101b of the body 101 and the front part 104 of the holding member 104/105. That is, the spring 106 is axially retained between a left side surface 104c of front part 104 of holding member 104/105 the inner wall 101b of the body 101. As a result, the spring 106 is caused to be compressed when the holding member 104/105 is moved back (i.e., to the right) to a retracted position relative to the body 101. As discussed above, the spring 106 causes (and/or biases) the holding member 104/105 towards an extended position once the trigger 109 is pressed. As a result, the holding member 104/105 cannot be moved back to a retracted position without causing the spring 106 to be compressed thereby.

As can be seen in FIG. 13, the front cap 103 has internal threads 103c and a planar inner annular surface 103d. The threads 103c are configured to engage external threads 102a of the intermediate section 102. The intermediate section 102 also includes an external cylindrical surface 102e and internal threads 102c which are configured to engage external threads 101c of the body 101. A cylindrical opening 102d is sized to receive (with a clearance) the front portion 104 so that contact can occur between stop surface FSS and stop surface MSS. In this regard, the stop surface FSS is an annular surface that is formed on an internal cylindrical projecting wall 102b which is integral with the section 102. Of course, this wall 102b can instead be formed by spaced apart projections which extend inwardly from the section 102. Alternatively, this wall 102b can be formed as a separate part and/or removable part (e.g., a snap ring), as in the embodiment shown in FIGS. 14-21. The front part 104 includes a small cylindrical section 104a which utilizes two oppositely arranged slots (similar to slots 4d in FIG. 6). The section 104a also has an internal opening (e.g., see 4f in FIG. 6) which is sized to receive the lancet 10. In order to ensure that the lancet 10 is securely and axially retained within opening, the front part 104 includes projections (e.g., see 4e in FIG. 6) which have sharp ends for gripping the lancet 10. The slots allow the opening to expand and contract with insertion and removal of the lancet 10 and allow the end 104 to act as two spring fingers. Front part 104 also includes larger cylindrical section 104g which can slide within openings 102d and 101a. In order to connect the front part 104 with the rear part 105 to form the holding member 104/105, the front part 104 includes internal threads which are configured to engage external threads of the rear part 1-5. The rear part 105 also has a cylindrical section 105c which is sized and configured to slide within (with a clearance) cylindrical opening 101d of body 101 and an enlarged cylindrical gripping end 105b.

FIGS. 14-21 show various views of still another embodiment of the lancet device. Lancet device LD has two main external parts, i.e., a lancet body 201 and a front cover or cap 203. These parts 201 and 203 are connected to each other via threads and/or a threaded connection when the lancet device LD is initially assembled. This embodiment also utilizes an optional dust or protective cap C. The cap C slides over the front cap or nut 203 and is retained thereon by frictional engagement therewith. Although, the cap C is shown with a cylindrical shape, the invention contemplates that the cap C can have any desired shape or configuration provided that it protects the lancet opening LO and plane P. A holding member 204/205 is movably disposed within the body 201. Also, a front cover or cap 203 is removably connected or attached to a front portion of the body 201. By removing the front cover 203, one can gain access to the lancet 10. The lancet 10 can thus be removed and replaced with a new lancet 10, as needed, once the front cover 203 is removed. As in many lancet devices, the lancet device LD defines a plane P which is configured to contact (i.e., be positioned against) a user's skin. Although not shown, the instant embodiment may utilize, e.g., a planar, an inwardly curved surface plane and an outwardly curved plane P beyond which the lancet need can extend. The lancet holder 204/205 has a rear portion 205, and specifically a gripping portion 205b, that can be gripped by a user. The front portion 204 and the rear portion 205 slide within the body 201. As will be described in more detail later on, movement of the gripping portion 205b rearwardly, causes the holding member 204/205 to retract until it reaches a spring loaded position shown in FIG. 17. The lancet 10, itself, is conventional and includes a needle. It can be removed and replaced with a new one, as is the case in many lancet devices. To ensure that lancet 10 is securely (yet removably) retained within the lancet device LD, the front portion 204 of the holding member 204/205 includes a lancet holding end 204a which receives the lancet 10 therein.

Figure 16:
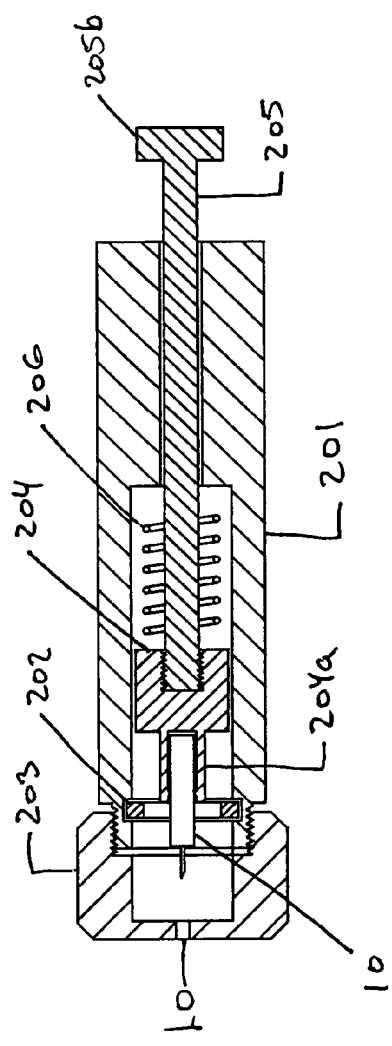
FIG. 16 shows a side cross-section view of the embodiment of FIG. 14. The device is shown with the lancet needle in an intermediate position prior to being pulled back and released. The lancet is not shown in cross-section.
Figure 17:
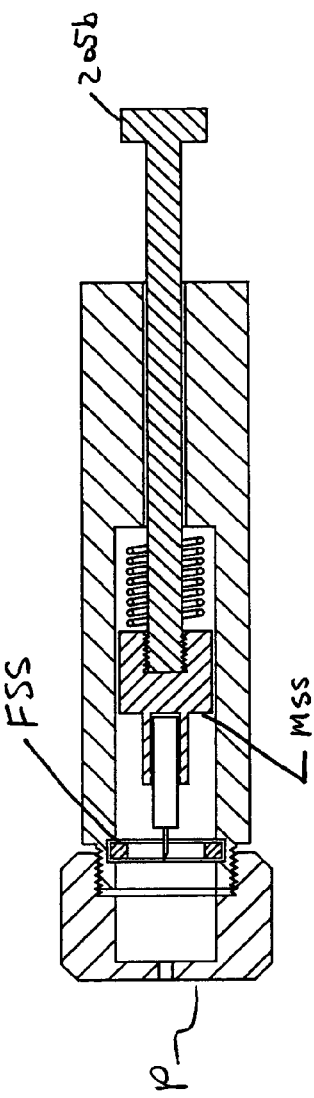
FIG. 17 shows a side cross-section view of the embodiment shown in FIG. 14. The device is shown with the lancet needle pulled back to a retracted position.

As can be seen in FIGS. 16 and 17, the holding member 204/205 arrangement preferably has a spring 206 mounted thereto. In this regard, the spring 206, which can be made of spring steel, is arranged to surround the holding member 204/205 in an area of the rear portion 205. Accordingly to one non-limiting example, the spring 206 has a diameter of approximately 6.2 mm, a freelength of approximately 36.7 mm, and a wire size of 0.5 mm. This spring 206 causes (and/or biases) the holding member 204/205 to move towards an extended position (see FIG. 18) once the holding member 204/205 is pulled back (see FIG. 17). When a user wishes to place the lancet device LD in the loaded position, a user need only move gripping portion 205b rearwardly until the holding member arrangement 204/205 reaches the position shown in FIG. 17. This, in turn, compresses the spring 206 to a certain extent. However, when the user releases the gripping portion 205b, spring 206 causes the holding member 204/205 to move to a fully extended position shown in FIG. 18. However, once contact occurs between stop surface MSS and stop surface FSS (see FIG. 18), the spring 206 causes the holding member 204/205 to automatically retract axially back into the body 201 to a position similar to that of FIG. 16. Although not shown, this occurs because the spring 206 has one end, i.e., the left end, coupled to the front portion 204 of the holding member 204/205 and another end, i.e., the right end, coupled to the annular surface 201b of the body 201. One way this can occur is shown in FIG. 46, which will be more fully described later on. The spring 206 can, of course, be connected to these parts in any desired manner. Alternatively, the spring 206 can be connected to these parts 204, 201 in a manner similar to that of FIG. 45, i.e., via flanges formed on the parts 201 and 204. In this way, the lancet needle only momentarily projects past the plane P in the extended position before it is caused to retract back in the lancet device by the spring 206. As a result, the lancet needle only projects past or beyond the plane P for a very brief time (i.e., a fraction of a second when the gripping end 205b is released) and is otherwise not exposed to a user while the front cover 203 is installed thereon. Accordingly, a user or other innocent bystanders can be protected from being injured unintentionally by an exposed needle.

The lancet device LD utilizes the front cap 203 to adjust the penetration depth of the lancet needle. The front cap 203 is preferably mounted to the body 201 (and optionally to an intermediate section of the type shown in FIG. 2 if this embodiment is modified to include such an intermediate section) of the body 201 so as to be at least partially rotate in each of two directions. Of course, the front cap 203 can be mounted to the body 201 in any desired manner (i.e., with or without threads) provided it functions properly in the intended manner, i.e., provided it moves axially forwards and backwards. To ensure that the front cap 203 is axially retained to body 201, yet allowed to rotate with respect to the lancet device body 201, the front cap 203 has internal threads 203c which engage external threads 201c of the body 201. The front cap 203 also includes chamfered corners 203b and raised projections 203a which allow a user to more securely grip the front cap 203. The body 201 has an internal recess 201e which is sized and configured to receive a snap ring 202 that includes a fixed stop surface FSS (see FIG. 17) which is configured to be engaged by a movable stop surface MSS (in particular annular stop surface MSS of front portion 204) that is formed on or coupled to the front portion 204 of holding member 204/205.

As described above, FIG. 17 shows the lancet device LD with the lancet member 204/205 in the loaded position, i.e., ready to move to an extended position (see FIG. 18) when the gripping end 205b is released. The holding member 204/205 retains the loaded position of FIG. 17 as long as the user continues to grip the gripping end 205b. On the other hand, FIG. 18 shows what happens when the user releases end 205b. That is, the holding member 204/205 is released from the loaded position of FIG. 17, and is caused to move towards plane P. This occurs because the holding member 204/205 is free to slide within body 201. As will be described later on with regard to other embodiments, the holding member 204/205 can also have a polygonal cross-section shape which corresponds to the polygonal opening 201d in the body 201 so as to ensure that the holding member 204/205 does not rotate while it moves axially back and forth. However, for this embodiment, it is sufficient if the holding member 204/205 has cylindrical outer surfaces (e.g., 204g and 205c) which slide within (with a clearance) cylindrical surfaces (e.g., 201a and 201d) in the body 201. Again, with regard to FIGS. 17 and 18, it can be seen that the holding member 204/205 can move towards the plane P until the stop surface MSS contacts or engages the stop surface FSS of the body 201, i.e., via snap ring 202. In this position, the needle of the lancet 10 projects past the plane P and through opening LO and thereby punctures the skin of a user which is resting against the plane P. The lancet device LD is then ready to be reloaded, i.e., it can then be placed back into the position shown in FIG. 17.

FIG. 18 shows the lancet device LD in one of the pre-set extended positions, i.e., in one of the positions of the front cap 203 that will cause a desired puncture depth in the skin of a user (not shown). The distance that the lancet needle projects past plane P is thus determined by rotating the front cap 203 until the desired setting is reached, e.g., arrow 208 lines up with one of the indicia 207. This setting, in turn, causes the plane P to move axially relative to fixed stop surface FSS. Since the movable stop surface MSS always contacts the fixed stop surface FSS in the extended position of the holding member 204/205, and since the plane P moves relative to the fixed stop surface FSS, adjustment of the front cap 203 (by rotation) causes a corresponding change in distance between plane P and the end of the lancet needle, e.g., the rotational position of the front cap 203 thus determines how much of the end of the lancet needle extends past the plane P. The depth setting is thus controlled by contact between the stop surface MSS, stop surface FSS and the rotational position of the front cap 203. FIG. 18 shows the needle tip projecting through the opening LO in the front cover 203 and past the plane P. Thereafter, the user can pull end 205b back to compress spring 206 to again arm the lancet device LD.

FIG. 18 shows a cross-section view of the lancet device of FIGS. 14-17 wherein the holding member 204/205 is in the fully extended position. In this regard, the holding member 204/205 has reached its maximum extended position caused by axial expansion of the spring 206. As in FIGS. 16 and 17, the front cover 203, spring 206, snap ring 202, lancet 10 and holding member 4/5 can be seen in their installed and/or assembled position. However, this figure allows one to more clearly see that the spring 206 is arranged to surround the holding member 204/205, just behind the lancet receiving front portion 204. The spring 206 is preferably sized to slide into internal opening 201a of the body 201. More particularly, the spring 206 is preferably disposed inside the body 201 and between an inner wall 201b of the body 201 and the front part 204 of the holding member 204/205. That is, the spring 206 is axially retained between a left side surface 204c of front part 204 of holding member 204/205 the inner wall 201b of the body 201. As a result, the spring 206 is caused to be compressed when the holding member 204/205 is moved back (i.e., to the right) to a retracted position relative to the body 201. As discussed above, the spring 206 causes (and/or biases) the holding member 204/205 towards an extended position once a gripping end 205b is released. As a result, the holding member 204/205 cannot be moved back to a retracted position without causing the spring 206 to be compressed thereby.

As can be seen in FIGS. 19-21, the front cap 203 has internal threads 203c and a planar inner annular surface 203d. The threads 203c are configured to engage external threads 201c of the body 201. Unlike the previous embodiments, this embodiment does not utilize an intermediate section. However, the invention contemplates that such an intermediate section could be utilized in this embodiment, in which case the intermediate section of FIG. 5 would be modified to replace projection 2b with a recess similar to 201e of FIG. 21. Similarly, the previous embodiments need not utilize an intermediate section, as in this embodiment, and instead utilize a snap ring and/or a two-piece body. A cylindrical opening 201a is sized to receive (with a clearance) the front portion 204 so that contact can occur between stop surface FSS and stop surface MSS. In this regard, the stop surface FSS is an annular surface that is formed on an internal cylindrical wall of the snap ring 202 which is axially retained in recess 201e. Of course, this wall can instead be formed by spaced projections which extend inwardly from the snap ring 202. Alternatively, the snap ring 202 can be replaced with a wall that is formed integrally with the body 201, as in the embodiment shown in, e.g., FIG. 1. The front part 204 includes a small cylindrical section 204a which utilizes two oppositely arranged slots 204d. The section 204a also has an internal opening 204f which is sized to receive the lancet 10. In order to ensure that the lancet 10 is securely and axially retained within opening 204f, the front part 204 includes projections 204e which have sharp ends for gripping the lancet 10. The slots 204d allow the opening 204f to expand and contract with insertion and removal of the lancet 10 and allow the end 204 to act as two spring fingers. Front part 204 also includes larger cylindrical section 204g which can slide within opening 201a. In order to connect the front part 204 with the rear part 205 to form the holding member 204/205, the front part 204 includes internal threads 204b which are configured to engage external threads 205a. The rear part 205 also has a cylindrical section 205c which is sized and configured to slide within (with a clearance) cylindrical opening 201d of body 201 and an enlarged cylindrical gripping end 205b. As with the previous embodiments, the holding member 204/205 can alternatively be formed as a one-piece member. Moreover, these parts can be connected in any desired manner other than threads.

FIGS. 22-28 show another embodiment of lancet device. Lancet device LD has a lancet body 301 which can be made as a one-piece member as with the embodiment shown in, e.g., FIGS. 1-7. Alternatively, it can be made as a two-piece structure as in the embodiment shown in, e.g., FIG. 39. Such body parts can, of course, be connected, e.g., using adhesives and/or fasteners and/or welding and/or snap-together holding mechanisms (not shown) to each other when the lancet device LD is initially assembled. A holding member 304/305 is movably disposed within the body 301. Also, a front cover 303 is removably connected or attached to an intermediate section 302 of the body. By removing the front cover 303, one can gain access to the lancet 10. The lancet 10 can thus be removed and replaced with a new lancet 10, as needed, once the front cover 303 is removed. As in many lancet devices, the lancet device LD defines a plane P which is configured to contact (i.e., be positioned against) a user's skin. However, unlike known lancet devices, the instant embodiment may utilize an inwardly curved and/or an outwardly curved surface plane P beyond which the lancet need can extend. The lancet holder 304/305 has a rear portion 305, and specifically a gripping portion 305b, that can be gripped by a user. The front portion 304 and a front portion of rear portion 305 slide within the body 301. As will be described in more detail later on, movement of the gripping portion 305b rearwardly, causes the holding member 304/305 to retract until it reaches a spring loaded position shown in FIG. 25. The lancet 10, itself, is conventional and includes a needle. It can be removed and replaced with a new one, as is the case in many lancet devices. To ensure that lancet 10 is securely (yet removably) retained within the lancet device LD, the front portion 304 of the holding member 304/305 includes a lancet holding end 304a which receives the lancet 10 therein.

Figure 24:
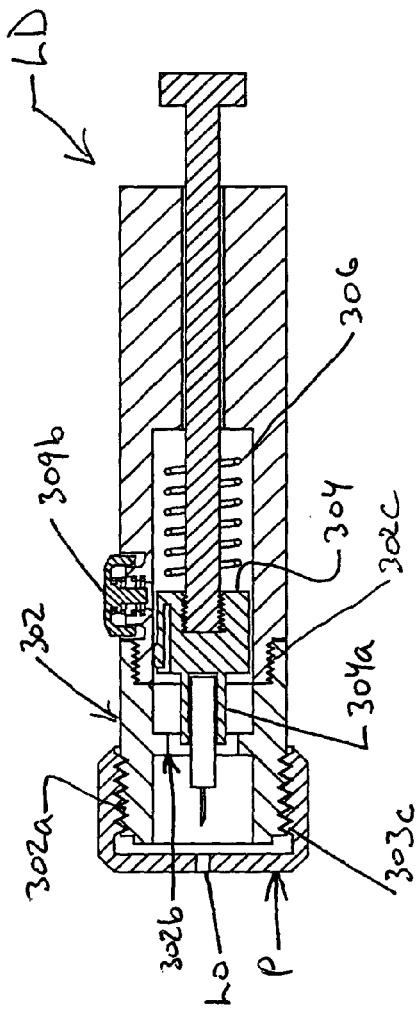
FIG. 24 shows a side cross-section view of the embodiment of FIG. 22. The device is shown with the lancet needle in an intermediate position prior to being pulled back and released. The lancet is not shown in cross-section.
Figure 25:
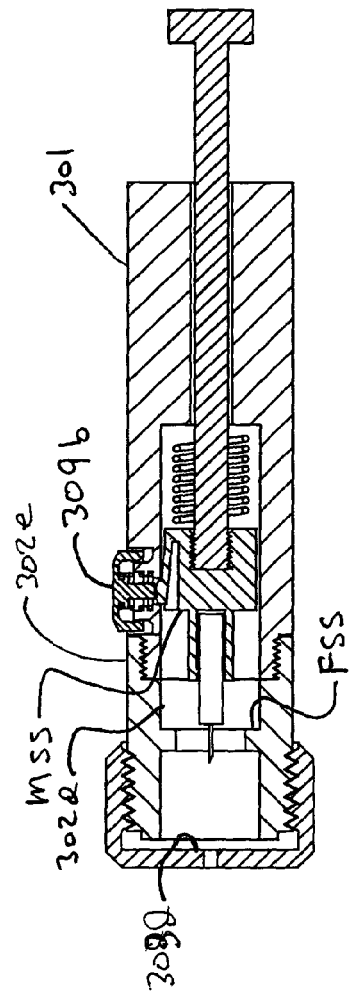
FIG. 25 shows a side cross-section view of the embodiment shown in FIG. 22. The device is shown with the lancet needle pulled back to a retracted position.

As can be seen in FIGS. 24 and 25, the holding member 304/305 arrangement preferably has a spring 306 mounted thereto. In this regard, the spring 306, which can be made of spring steel, is arranged to surround the holding member 304/305, just behind the front portion 304. By way of one non-limiting example, the spring 306 may have a diameter of approximately 6.2 mm, a freelength of approximately 36.7 mm, and a wire size of 0.5 mm. This spring 306 causes (and/or biases) the holding member 304/305 to move towards an extended position once a trigger 309 is activated (not shown). The trigger 309 includes a portion 309a that extends into the body 301, and is mounted to the body 301. The trigger 309 also has a finger engaging (e.g. push button) portion 309b that can be pushed and/or deflected into the lancet device LD. The trigger 309 also utilizes a spring 311 which biases the trigger 309 towards the position shown in, e.g., FIG. 24. Thus, when force is applied to the finger engaging portion 309b, the inner portion 309a moves into contact with deflecting member 304h of the front portion 304. This causes the deflecting member 304h to disengage from the opening 301h of the body 301, which allows member 304 to move towards plane P under the action of the spring 306. On the other hand, when the push button 309b is released, the trigger 309 is capable of returning to the position shown in FIG. 24.

As discussed above, the spring 306 causes (and/or biases) the holding member 304/305 to move towards an extended position (not shown) once the holding member 304/305 is pulled back (see FIG. 25). When a user wishes to place the lancet device LD in the loaded or armed position, a user need only move gripping portion 305b rearwardly until the holding member arrangement 304/305 reaches the position shown in FIG. 25. This, in turn, compresses the spring 306 to a certain extent and allows deflecting member 304h to catch or engage the opening 301h. Such engagement ensures that the front portion 304 is prevented from moving axially towards the plane P until the trigger 309 is depressed. However, when the user presses the trigger 309, the deflecting member 304h is moved out of engagement with opening 301h and the spring 306 causes the holding member 304/305 to move to a fully extended position. However, once contact occurs between stop surface MSS and stop surface FSS, the spring 306 causes the holding member 304/305 to automatically retract axially back into the body 301 to a position similar to that of FIG. 24. Although not shown, this occurs because the spring 306 has one end, i.e., the left end, coupled to the front portion 304 of the holding member 304/305 and another end, i.e., the right end, coupled to the annular surface 301b of the body 301. One way this can occur is shown in FIG. 46, which will be more fully described later on. The spring 306 can, of course, be connected to these parts in any desired manner. Alternatively, the spring 306 can be connected to these parts 301, 304 in a manner similar to that of FIG. 45, i.e., via flanges formed on the parts 301 and 304. In this way, the lancet needle only momentarily projects past the plane P in the extended position before it is caused to retract back in the lancet device by the spring 306. As a result, the lancet needle only projects past or beyond the plane P for a very brief time (i.e., a fraction of a second when the trigger 309 is released) and is otherwise not exposed to a user while the front cover 303 is installed thereon. Accordingly, a user or other innocent bystanders can be protected from being injured unintentionally by an exposed needle.

As was the case in the previous embodiments, the lancet device LD utilizes the front cap 303 to adjust the penetration depth of the lancet needle. The front cap 303 is preferably mounted to the body 301 and/or to the intermediate section 302 of the body 301 so as to be at least partially rotate in each of two directions. Of course, the front cap 303 can be mounted to the body 301 in any desired manner (i.e., with or without threads) provided it functions properly in the intended manner, i.e., provided it moves axially forwards and backwards. To ensure that the front cap 303 is axially retained to body parts 302 and 303, yet allowed to rotate with respect to the lancet device body, the front cap 303 has internal threads 303c which engage external threads 302a of the intermediate section 302. The front cap 303 also includes chamfered corners 303b and raised projections 303a which allow a user to more securely grip the front cap 303. The intermediate body section 302 has an internal projecting wall 302b that includes a fixed stop surface FSS which is configured to be engaged by a movable stop surface MSS (in particular stop surface MSS of front portion 304) that is formed on or coupled to the front portion 304 of holding member 304/305.

As described above, FIG. 25 shows the lancet device LD with the lancet member 304/305 in the loaded position, i.e., ready to move to an extended position when the trigger 309 is depressed. The holding member 304/305 retains the loaded position of FIG. 25 as long as the user does not press the trigger 309. As in one of the previous embodiments, when the user presses the trigger 309, the holding member 304/305 is released from the loaded position of FIG. 25, and is caused to move towards plane P. This occurs because the holding member 304/305 is free to slide within body 301. As will be described later on with regard to other embodiments, the holding member 304/305 can also have a polygonal cross-section shape which corresponds to a polygonal opening 301d in the body 301 so as to ensure that the holding member 304/305 does not rotate while it moves axially back and forth. However, for this embodiment, it is sufficient if the holding member 304/305 has cylindrical outer surfaces (e.g., 304g and 305c) which slide within (with a clearance) cylindrical surfaces (e.g., 301a, 302d, and 301d) in the body 301 and intermediate section 302. As with the previous embodiments, it can be recognized that the holding member 304/305 can move towards the plane P until the stop surface MSS contacts or engages the stop surface FSS of the intermediate section 302. In this position, the needle of the lancet 10 projects past the plane P and through opening LO and thereby punctures the skin of a user which is resting against the plane P. The lancet device LD is then ready to be reloaded, i.e., it can then be placed back into the position shown in FIG. 25.

As with the other embodiments, the lancet device LD can have ant desired number of pre-set extended positions, i.e., in one of the positions of the front cap 303 that will cause a desired puncture depth in the skin of a user (not shown). The distance that the lancet needle projects past plane P is thus determined by rotating the front cap 303 until the desired setting is reached, e.g., arrow 308 lines up with one of the indicia 307. This setting, in turn, causes the plane P to move axially relative to fixed stop surface FSS. Since the movable stop surface MSS always contacts the fixed stop surface FSS in the extended position of the holding member 304/305, and since the plane P moves relative to the fixed stop surface FSS, adjustment of the front cap 303 (by rotation) causes a corresponding change in distance between plane P and the end of the lancet needle, e.g., the rotational position of the front cap 303 thus determines how much of the end of the lancet needle extends past the plane P. The depth setting is thus controlled by contact between the stop surface MSS, stop surface FSS and the rotational position of the front cap 303. As with the previous embodiments, the needle tip can project through the opening LO in the front cover 303 and past the plane P. Thereafter, the user can pull end 305b back to compress spring 306 to again arm the lancet device LD. In this regard, the engaging portion 309a of trigger 309 utilizes an engaging surface which, when engaged with the deflecting member 304h of the front portion 104, causes the front portion 304 to move. The trigger 309 can be moved against the biasing force of a trigger spring 311. To ensure that the trigger 309 is retained on the body 301, the spring 311 has an upper end which is retained on a flange 309c of the trigger 309 and a lower end that is retained to a flange 301g of the body 301. An annular opening 301e is formed in the body 301 and is sized and configured to receive an outer flange portion 309d of the trigger 309. Of course, the invention contemplates other configurations of the trigger 309 and the invention is not limited to any particular type of trigger.

Figure 22:
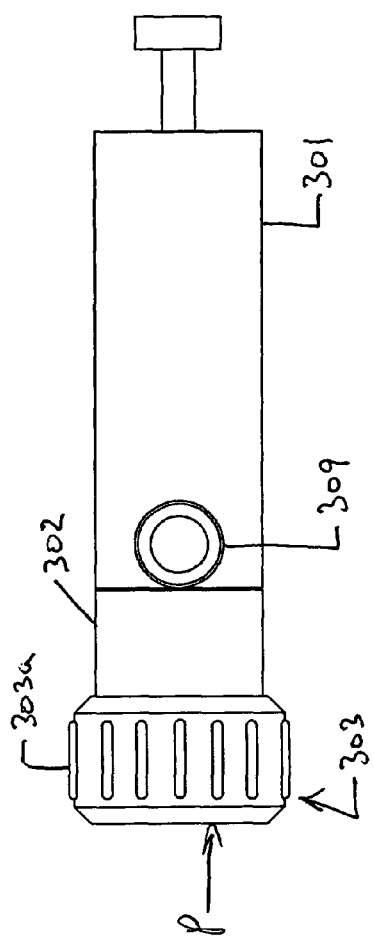
FIG. 22 shows a top view of another embodiment of the lancet device. This embodiment utilizes a push-button trigger.
Figure 23:
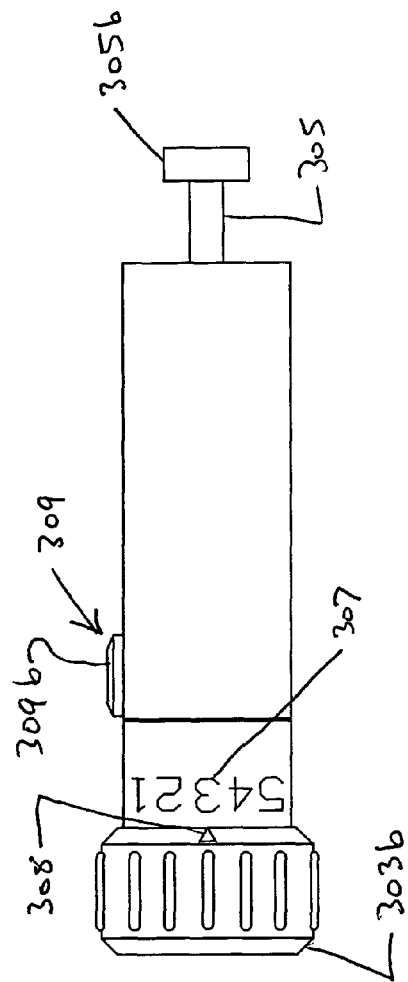
FIG. 23 shows a side view of the embodiment shown in FIG. 22.

FIG. 24 shows a cross-section view of the lancet device of FIGS. 22 and 23 wherein the holding member 304/305 is in an intermediate position. In this regard, the holding member 304/305 has not yet reached its maximum extended position caused by axial expansion of the spring 306. The front cover 303, intermediate body 302, spring 306, lancet 10 and holding member 304/305 can be seen in their installed and/or assembled position. However, this figure allows one to more clearly see that the spring 306 is arranged to surround the holding member 304/305, just behind the lancet receiving front portion 304. The spring 306 is preferably sized to slide into internal opening 301a of the body 301. More particularly, the spring 306 is preferably disposed inside the body 301 and between an inner annular wall 301b of the body 301 and the front part 304 of the holding member 304/305. That is, the spring 306 is axially retained between a left side surface 304c of front part 304 of holding member 304/305 the inner wall 301b of the body 301. As a result, the spring 306 is caused to be compressed when the holding member 304/305 is moved back (i.e., to the right) to a retracted position relative to the body 301. As discussed above, the spring 306 causes (and/or biases) the holding member 304/305 towards an extended position once the trigger 309 is pressed. As a result, the holding member 304/305 cannot be moved back to a retracted position without causing the spring 306 to be compressed thereby.

As can be seen in FIGS. 24-28, the front cap 303 has internal threads 303c and a planar inner annular surface 303d. The threads 303c are configured to engage external threads 302a of the intermediate section 302. The intermediate section 302 also includes an external cylindrical surface 302e and internal threads 302c which are configured to engage external threads 301c of the body 301. A cylindrical opening 302d is sized to receive (with a clearance) the front portion 304 so that contact can occur between stop surface FSS and stop surface MSS. In this regard, the stop surface FSS is an annular surface that is formed on an internal cylindrical projecting wall 302b which is integral with the section 302. Of course, this wall 302b can instead be formed by spaced apart projections which extend inwardly from the section 302. Alternatively, this wall 302b can be formed as a separate part and/or removable part (e.g., a snap ring), as in the embodiment shown in FIG. 16. The front part 304 includes a small cylindrical section 304a which utilizes two oppositely arranged slots (see FIG. 26). The section 304a also has an internal opening (e.g., see 304f in FIG. 26) which is sized to receive the lancet 10. In order to ensure that the lancet 10 is securely and axially retained within opening, the front part 304 includes projections (e.g., see 304e in FIG. 26) which have sharp ends for gripping the lancet 10. The slots 304d allow the opening 304f to expand and contract with insertion and removal of the lancet 10 and allow the end 304 to act as two spring fingers. Front part 304 also includes larger cylindrical section 304g which can slide within openings 302d and 301a. The front part 304 also includes the deflecting member 304h which is formed integrally therewith. In this regard, deflecting member 304h and the front part 304 are formed of a material which allows the deflecting member 304h to act as a spring in that it can be deflected inwards (compare FIGS. 24 and 25) and thereafter return to an undeflected position (see FIG. 25). In order to connect the front part 304 with the rear part 305 to form the holding member 304/305, the front part 304 includes internal threads which are configured to engage external threads of the rear part 305. The rear part 305 also has a cylindrical section 305c which is sized and configured to slide within (with a clearance) cylindrical opening 301d of body 301 and an enlarged cylindrical gripping end 305b. As with the previous embodiments, the holding arrangement 304/305 can alternatively be formed as a one-piece member. Moreover, the intermediate section 302 and body 301 can also alternatively be formed as a one-piece member as in the embodiment shown in FIGS. 14-21.

FIGS. 29-35 show another embodiment of lancet device. Lancet device LD has a lancet body 401 which can be made as a one-piece member as with the embodiment shown in FIGS.

1-7. Alternatively, it can be made as a two-piece structure as in the embodiment shown in, e.g., FIG. 39. Such body parts can, of course, be connected, e.g., using adhesives and/or fasteners and/or welding and/or snap-together holding mechanisms (not shown) to each other when the lancet device LD is initially assembled. A holding member 404/405 is movably disposed within the body 401. Also, a front cover 403 is removably connected or attached to an intermediate section 402 of the body. By removing the front cover 403, and optionally the intermediate section 302, one can gain access to the lancet 10. The lancet 10 can thus be removed and replaced with a new lancet 10, as needed, once the front cover 403 is removed. As in many lancet devices, the lancet device LD defines a plane P which is configured to contact (i.e., be positioned against) a user's skin. However, unlike known lancet devices, the instant embodiment may utilize an inwardly curved and/or an outwardly curved surface plane P beyond which the lancet need can extend. The lancet holder 404/405 has a rear portion 405, and specifically a locking portion 405b, that can be engaged by a locking member 414 after a back cap retracting spring 415 is mounted to the member 405. The front portion 404 and the rear portion 405 slide within the body 401. As will be described in more detail later on, movement of the locking portion 405b rearwardly (see FIG. 33), causes the holding member 404/405 to retract until it reaches a spring loaded position shown in FIGS. 32 and 33. The lancet 10, itself, is conventional and includes a needle. It can be removed and replaced with a new one, as is the case in many lancet devices. To ensure that lancet 10 is securely (yet removably) retained within the lancet device LD, the front portion 404 of the holding member 404/405 includes a lancet holding end 404a which receives the lancet 10 therein.

As can be seen in FIGS. 31 and 32, the holding member 404/405 arrangement preferably has a first spring 406 mounted thereto. In this regard, the first spring 406, which can be made of spring steel, is arranged to surround the holding member 404/405, just behind the front portion 404. By way of one non-limiting example, the spring 406 may have a diameter of approximately 6.2 mm, a freelength of approximately 36.7 mm, and a wire size of 0.5 mm. This spring 406 causes (and/or biases) the holding member 404/405 to move towards an extended position once a trigger 409 is activated (not shown). The trigger 409 includes a portion 409a that extends into the body 401, and is mounted to the body 401. The trigger 409 also has a finger engaging (e.g. push button) portion 409b that can be pushed and/or deflected into the lancet device LD. The trigger 409 also utilizes a spring 411 which biases the trigger 409 towards the position shown in FIGS. 31-33. Thus, when force is applied to the finger engaging portion 409b, the inner portion 409a moves into contact with deflecting member 404h of the front portion 404. This causes the deflecting member 404h to disengage with opening 401h, which allows front part 404 to move towards plane P. On the other hand, when the push button 409b is released, the trigger 409 is capable of returning to the position shown in FIGS. 31-33.

As discussed above, the spring 406 causes (and/or biases) the holding member 404/405 to move towards an extended position (not shown) once the holding member 404/405 is pulled back (see FIG. 33) using the back cap 412. When a user wishes to place the lancet device LD in the loaded position (see FIG. 32), a user need only move the back cap 412 rearwardly until the holding member arrangement 404/405 reaches the position shown in FIG. 33. This, in turn, compresses the first spring 406 to a certain extent and allows deflecting member 404h to catch or engage opening 401h. Such engagement ensures that the front portion 404 is prevented from moving axially towards the plane P until the trigger 409 is depressed. However, when the user presses the trigger 409, the deflecting member 404h is moved out of engagement with opening 401h and the spring 406 causes the holding member 404/405 to move to a fully extended position. However, once contact occurs between stop surface MSS and stop surface FSS, the spring 406 causes the holding member 404/405 to automatically retract axially back into the body 401 to a position similar to that of FIG. 31. Although not shown, this occurs because the spring 406 has one end, i.e., the left end, coupled to the front portion 404 of the holding member 404/405 and another end, i.e., the right end, coupled to the annular surface 401b of the body 401. One way this can occur is shown in FIG. 46, which will be more fully described later on. The spring 406 can, of course, be connected to these parts in any desired manner. Alternatively, the spring 406 can be connected to these parts 401, 404 in a manner similar to that of FIG. 45, i.e., via flanges formed on the parts 401 and 404. Of course, in this embodiment it is not necessary that the spring 406 be connected to parts 404 and 401. This is because this embodiment uses a second spring 415 to cause the holding member 404/405 to automatically retract after it reaches the fully extended position, i.e., a position in which stop surface MSS contacts stop surface FSS. To ensure that this occurs, the second spring 415 is able to compress with a force that is far less that the force needed to compress spring 406. Preferably, the spring 415 has a diameter of approximately 10.1 mm, a freelength of approximately 13.6 mm, and a wire size of 0.25 mm. In this way, the lancet needle only momentarily projects past the plane P in the extended position before it is caused to retract back in the lancet device by the spring 415. As a result, the lancet needle only projects past or beyond the plane P for a very brief time (i.e., a fraction of a second when the trigger 409 is released) and is otherwise not exposed to a user while the front cover 403 is installed thereon. Accordingly, a user or other innocent bystanders can be protected from being injured unintentionally by an exposed needle.

As was the case in the previous embodiments, the lancet device LD utilizes the front cap 403 to adjust the penetration depth of the lancet needle. The front cap 403 is preferably mounted to the body 401 and/or to the intermediate section 402 of the body 401 so as to be at least partially rotate in each of two directions. Of course, the front cap 403 can be mounted to the body 401 in any desired manner (i.e., with or without threads) provided it functions properly in the intended manner, i.e., provided it moves axially forwards and backwards. To ensure that the front cap 403 is axially retained to body parts 402 and 403, yet allowed to rotate with respect to the lancet device body, the front cap 403 has internal threads 403c which engage external threads 402a of the intermediate section 402. The front cap 403 also includes chamfered corners 403b and raised projections 403a which allow a user to more securely grip the front cap 403. The intermediate body section 402 has an internal projecting wall 402b that includes a fixed stop surface FSS (see FIG. 32) which is configured to be engaged by a movable stop surface MSS (in particular stop surface MSS of front portion 404) that is formed on or coupled to the front portion 404 of holding member 404/405.

As described above, FIG. 32 shows the lancet device LD with the lancet member 404/405 in the loaded position, i.e., ready to move to an extended position when the trigger 409 is depressed. The holding member 404/405 retains the loaded position of FIG. 32 as long as the user does not press the trigger 409. As in some of the previous embodiments, when the user presses the trigger 409, the holding member 404/405 is released from the loaded position of FIG. 32, and is caused to move towards plane P. This occurs because the holding member 404/405 is free to slide within body 401. As will be described later on with regard to other embodiments, the holding member 404/405 can also have a polygonal cross-section shape which corresponds to a polygonal opening 401d in the body 401 so as to ensure that the holding member 404/405 does not rotate while it moves axially back and forth. However, for this embodiment, it is sufficient if the holding member 404/405 has cylindrical outer surfaces (e.g., 404g and 405c) which slide within (with a clearance) cylindrical surfaces (e.g., 401a, 402d, and 401d) in the body 401 and intermediate section 402. As with the previous embodiments, it can be recognized that the holding member 404/405 can move towards the plane P until the stop surface MSS contacts or engages the stop surface FSS of the intermediate section 402. In this position, the needle of the lancet 10 projects past the plane P and through opening LO and thereby punctures the skin of a user which is resting against the plane P. The lancet device LD is then ready to be reloaded, i.e., it can then be placed back into the position shown in FIG. 32.

As with the other embodiments, the lancet device LD can have any desired number of pre-set extended positions, i.e., in one of the positions of the front cap 403 that will cause a desired puncture depth in the skin of a user (not shown). The distance that the lancet needle projects past plane P is thus determined by rotating the front cap 403 until the desired setting is reached, e.g., arrow 408 lines up with one of the indicia 407. This setting, in turn, causes the plane P to move axially relative to fixed stop surface FSS. Since the movable stop surface MSS always contacts the fixed stop surface FSS in the extended position of the holding member 404/405, and since the plane P moves relative to the fixed stop surface FSS, adjustment of the front cap 403 (by rotation) causes a corresponding change in distance between plane P and the end of the lancet needle, e.g., the rotational position of the front cap 403 thus determines how much of the end of the lancet needle extends past the plane P. The depth setting is thus controlled by contact between the stop surface MSS, stop surface FSS and the rotational position of the front cap 403. As with the previous embodiments, the needle tip can project through the opening LO in the front cover 403 and past the plane P. Thereafter, the user can pull end 405b back, i.e., by pulling back cap 412 back, to compress spring 406 to again arm the lancet device LD. Of course, this movement of the back cap 412 causes the second spring 415 to compress (see FIG. 33). Once the holding member 404/405 is in the loaded position (see FIG. 32) the second spring 415 causes the back cap 412 to retract back into the body 401. In this regard, the engaging portion 409a of trigger 309 utilizes an engaging surface which, when engaged with the deflecting member 404h of the front portion 404, causes the front portion 404 to move. The trigger 409 also moves against the biasing force of a trigger spring 411. The spring 411 has an upper end which is retained on a flange 409c of the trigger 409 and a lower end that is retained to a flange 401g of the body 401. An annular opening 401e is formed in the body 401 and is sized and configured to receive an outer flange portion 409d of the trigger 409. Of course, the invention contemplates other configurations of the trigger 409 and the invention is not limited to any particular type of trigger.

Figure 33:
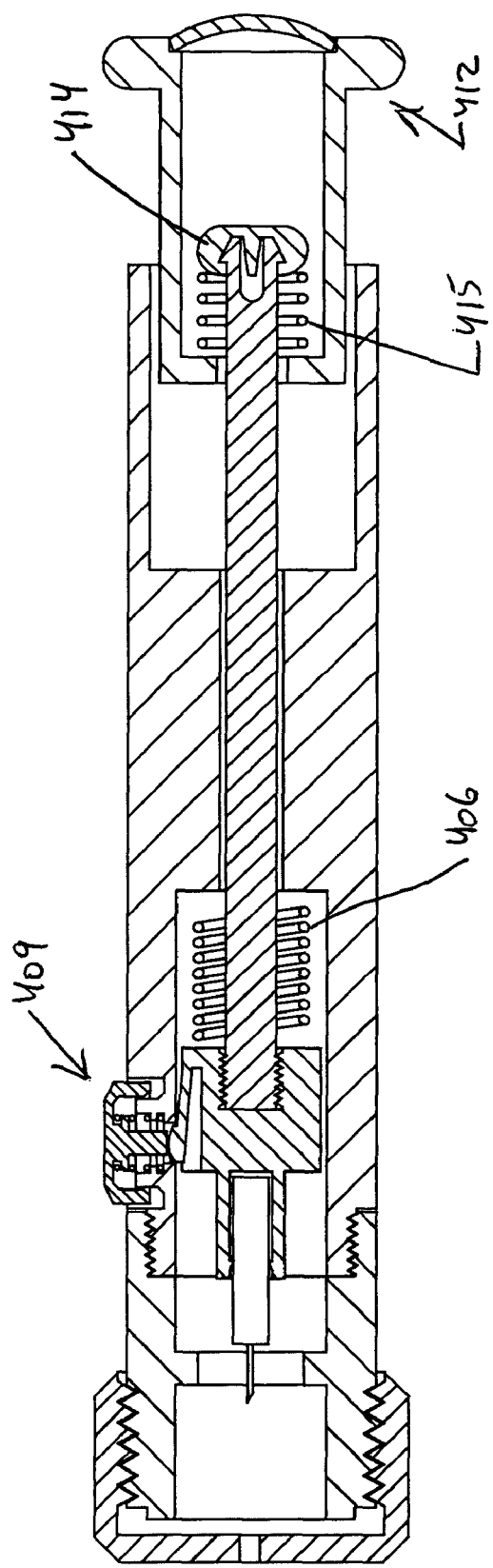
FIG. 33 shows an enlarged side cross-section view of the embodiment shown in FIG. 29. The device is shown with the lancet needle being pulled back to a retracted position by the back cap or arming mechanism.

FIG. 33 shows an enlarged cross-section view of the lancet device LD wherein the holding member 404/405 is in the loaded position. In this regard, the holding member 404/405 is ready for movement to its maximum extended position caused by axial expansion of the spring 406. The front cover 403, intermediate body 402, spring 406, lancet 10, spring 415, locking member 414, back cap 412 and holding member 404/405 can be seen in their installed and/or assembled position. However, this figure allows one to more clearly see that the springs 406 and 415 are arranged to surround the holding member 404/405, behind the lancet receiving front portion 404. The spring 406 is preferably sized to slide into internal opening 401a of the body 401, whereas the spring 415 is sized to slide into internal opening 401i of body 401.

The spring 406 is preferably disposed inside the body 401 and between an inner wall 401b of the body 401 and the front part 404 of the holding member 404/405. That is, the spring 406 is axially retained between a left side surface 404c of front part 404 of holding member 404/405 the inner wall 401b of the body 401. As a result, the spring 406 is caused to be compressed when the holding member 404/405 is moved back (i.e., to the right) to a retracted position relative to the body 401. As discussed above, the spring 406 causes (and/or biases) the holding member 404/405 towards an extended position once the trigger 409 is pressed. As a result, the holding member 404/405 cannot be moved back to a retracted position without causing the spring 406 to be compressed thereby.

The spring 415 is preferably disposed inside the body 401 and between an inner wall 412b of the back cap 412 and the end 405b of the holding member 404/405. That is, the spring 415 is axially retained between a left side surface 412c of the back cap 412 and locking member 414. As a result, the spring 415 is caused to be compressed when the holding member 404/405 is moved forward (i.e., to the left) to an extended position and when the back cap 412 is moved to an extended position (i.e., to the right) relative to the body 401. As discussed above, the spring 415 causes (and/or biases) the back cap 412 towards a retracted position once the back cap 412 is released. As a result, the back cap 412 cannot be moved away from the body 401 without causing the spring 415 to be compressed thereby. In order to allow the end 405b to extend into an internal opening 412f of the back cap 412, an opening 412d is provided in wall 412b. The back cap 412 also includes a recess 412g which is sized and configured to receive an end plug 413. To ensure that the back cap 412 can slide into opening 401i of the body 401, the back cap 412 includes a cylindrical outer surface 412e which is sized and configured to slide (with a clearance) within cylindrical opening 401i. A shoulder 412a is provided to allow the user to grip the back cap 412. The shoulder 412a also acts to limit the retraction of the back cap 412 into the body 401 by engaging end 401k in the fully retracted position.

As can be seen in FIG. 34 (note that the springs 406 and 415 have been removed for the sake of clarity), the front cap 403 has internal threads 403c and a planar inner annular surface 403d. The threads 403c are configured to engage external threads 402a of the intermediate section 402. The intermediate section 402 also includes an external cylindrical surface 402e and internal threads 402c which are configured to engage external threads 401c of the body 401. A cylindrical opening 402d is sized to receive (with a clearance) the front portion 404 so that contact can occur between stop surface FSS and stop surface MSS (not shown). In this regard, the stop surface FSS is an annular surface that is formed on an internal cylindrical projecting wall 402b which is integral with the section 402. Of course, this wall 402b can instead be formed by spaced apart projections which extend inwardly from the section 402. Alternatively, this wall 402b can be formed as a separate part and/or removable part (e.g., a snap ring), as in the embodiment shown in FIGS. 14-21.

The front part 404 includes a small cylindrical section 404a which utilizes two oppositely arranged slots (see FIG. 34). The section 404a also has an internal opening 404f which is sized to receive the lancet 10. In order to ensure that the lancet 10 is securely and axially retained within opening, the front part 404 includes projections 404e which have sharp ends for gripping the lancet 10. The slots 404d allow the opening 404f to expand and contract with insertion and removal of the lancet 10 and allow the end 404 to act as two spring fingers. Front part 404 also includes larger cylindrical section 404g which can slide within openings 402d and 401a. The front part 404 also includes the deflecting member 404h which is formed integrally therewith. In this regard, deflecting member 404h and the front part 404 is formed of a material which allows the deflecting member 404h to act as a spring in that it can be deflected inwards (compare FIGS. 31 and 32) and thereafter return to an undeflected position (see FIG. 32). In order to connect the front part 404 with the rear part 405 to form the holding member 404/405, the front part 404 includes internal threads 404b which are configured to engage external threads 405a of the rear part 405. The rear part 405 also has a cylindrical section 405c which is sized and configured to slide within (with a clearance) cylindrical opening 401d of body 401 and an enlarged locking end 405b whose barbs engage an internal opening in locking member 414.

Figure 36:
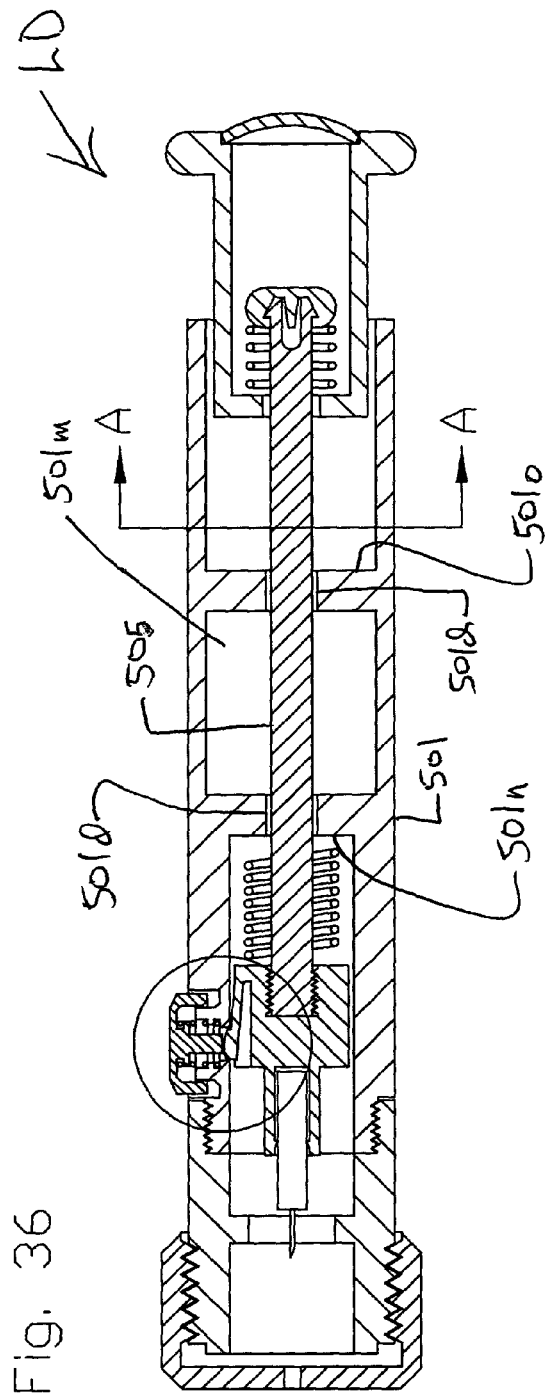
FIG. 36 shows a side cross-section view of still another embodiment of the lancet device. This embodiment is similar to the embodiment shown in FIG. 29, except that the rear portion of the lancet holding member utilizes a cross-shaped cross-section and the body uses internal projecting walls with cross-shaped openings. The device is shown with the lancet needle pulled back to a retracted position and with the back cap held in the extended position.
Figure 38:
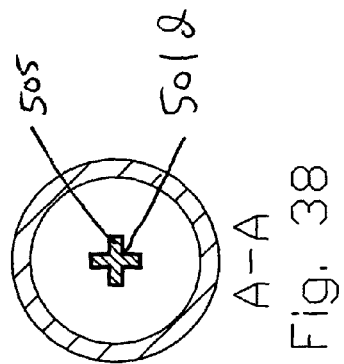
FIG. 38 shows a section view of the arrows A-A shown in FIG. 36. The cross-shaped opening and the cross-shaped cross-section of rear portion of the holding member is shown.
Figure 37:
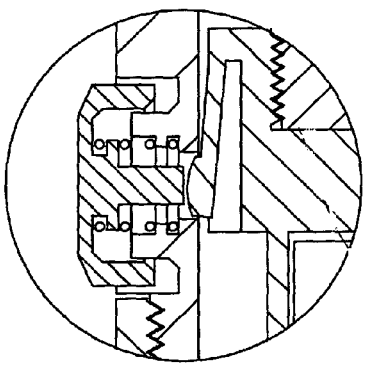
FIG. 37 shows an enlarged partial section view of the trigger used in the embodiment shown in FIG. 36.

FIGS. 36-38 show another embodiment of lancet device. Lancet device LD has a lancet body 501 which can be made as a one-piece member as with the embodiment shown in, e.g., FIGS. 1-7. Alternatively, it can be made as a two-piece structure as in the embodiment shown in, e.g., FIG. 39. Such body parts can, of course, be connected, e.g., using adhesives and/or fasteners and/or welding and/or snap-together holding mechanisms (not shown) to each other when the lancet device LD is initially assembled. The parts other than the body 501 can be the same as those used in the embodiment shown in FIGS. 29-35. Accordingly, the details of these parts will not be described again. However, the rear holding member 505 in this embodiment may also be different in that it may utilize a polygonal configuration which can be in the form of a cross (see FIG. 38). To ensure that the rear portion 505 is supported in the body 501, two support walls 501n and 501o extend inwards into the body 501. An enlarged opening 50m is provided between walls 501n and 501o. The walls 501n and 501o also include openings 501d which are sized and configured (with a clearance) to slidingly receive the rear portion 505. The lancet device LD will otherwise function in an manner similar to that of FIGS. 29-35.

Figure 39:
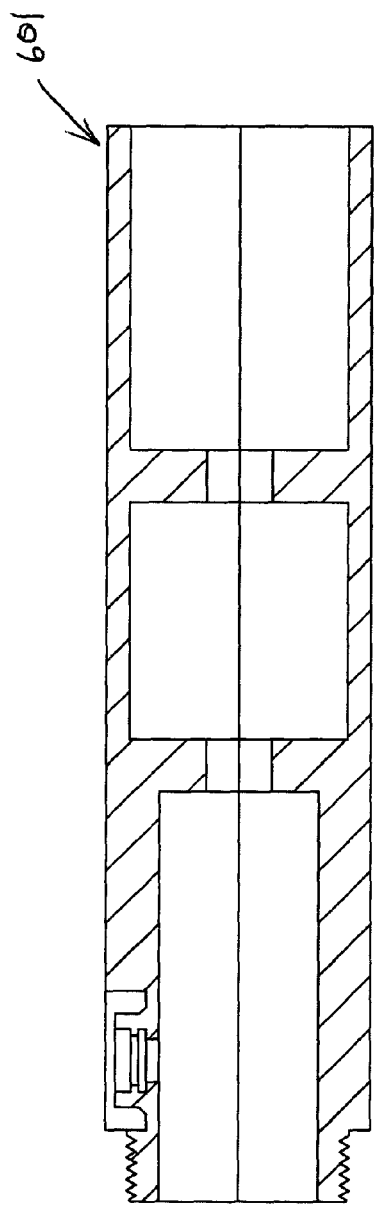
FIG. 39 shows an enlarged side cross-section view of an alternative two-piece body which used in the embodiment shown in FIG. 36.
Figure 40:
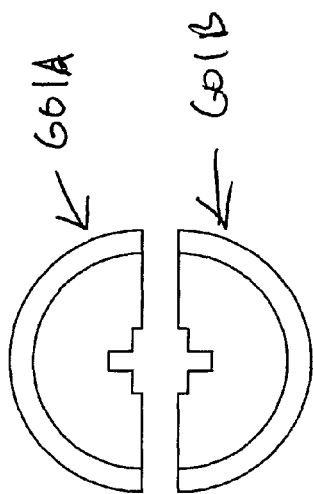
FIG. 40 shows a rear view of the two-piece body shown in FIG. 39. The two body parts are shown disassembled.

FIGS. 39-40 show an embodiment of a lancet device body 601 which can be used in the embodiment shown in FIGS. 36-38. The body 601 is the same as that shown in FIGS. 36-38 except that it is made as a two-piece structure. In this regard, the body 601 an upper part 601A and a lower part 601B which can be connected together in any desired manner. Such body parts can, of course, be connected, e.g., using adhesives and/or fasteners and/or welding and/or snap-together holding mechanisms (not shown) to each other when the lancet device LD is initially assembled. The use of a two-piece body, similar to that one shown herein, can be used in any of the disclosed embodiments.

FIGS. 41-42 show an embodiment of a lancet device which utilizes a rear portion 705 of the lancet holding arrangement that includes two oppositely arranged stop projections 705A and 705B. Such an arrangement may be used on the embodiments shown in FIGS. 29-38. The purpose of the stop projections 705A and 705B is to prevent the second spring 715 from compressing completely and to ensure that the back cap 712 is not pulled out from the body 701 beyond a desired amount. In this regard, when the back cap 712 is pulled back (i.e., to the right), the surface 712c contacts the stop projections 705A and 705B and the spring 715 is prevented from further compression. Once such contact occurs, the holding member 705 begins to move backwards with the back cap 712 in the manner similar to that described with regard to FIGS. 29-38.

Figure 43:
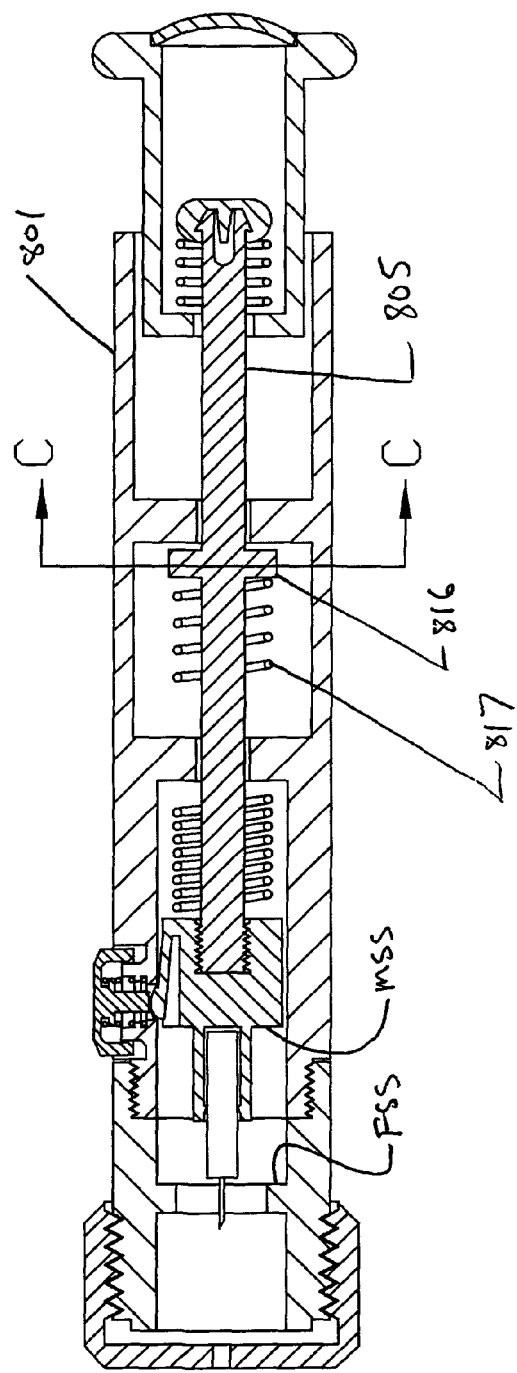
FIG. 43 shows a side cross-section view of still another embodiment of the lancet device. This embodiment is similar to the embodiment shown in FIG. 36, except that it uses the two-piece body shown in FIG. 39, a middle spring and the lancet holding member utilizes a protruding wall. The device is shown with the lancet needle pulled back to a retracted position and with the back cap held in the extended position.
Figure 44:
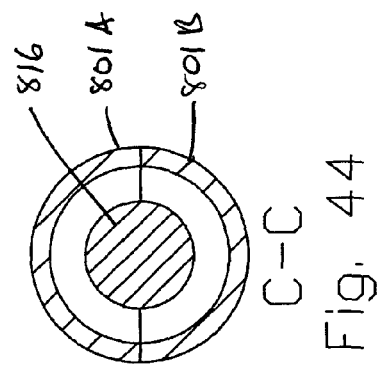
FIG. 44 shows a section view of the arrows C-C shown in FIG. 43. The protruding wall of rear portion of the holding member is shown.

FIGS. 43-44 show another embodiment of lancet device. Lancet device LD has a lancet body 801 which can be made as a two-piece member as with the embodiment shown in FIGS. 39-40. Alternatively, it can be made as a one-piece structure as in the embodiment shown in, e.g., FIGS. 36-38. Such body parts can, of course, be connected, e.g., using adhesives and/or fasteners and/or welding and/or snap-together holding mechanisms (not shown) to each other when the lancet device LD is initially assembled. The parts other than the body 801 and the rear holding member 805 can be the same as those used in the embodiment shown in FIGS. 36-38. Accordingly, the details of these parts will not be described again. The rear holding member 805 in this embodiment utilizes both a polygonal configuration which can be in the form of a cross (see FIG. 38) and a projecting portion 816. To ensure that the holding arrangement is automatically retracted after the stop surface MSS contacts stop surface FSS, a third spring 817 is provided. The third spring 817 is arranged an wall of the body 801 and the projecting part 816. The third spring 817 can be similar to that of the back cap spring. As in the embodiment shown in FIGS. 36-40, the walls of the body 801 include openings which are sized and configured (with a clearance) to slidingly receive the rear portion 805. The lancet device LD will function in an manner similar to that of FIGS. 29-35, except that the third spring 816 will also aid in retracting the lancet holding member after the stop surface MSS contacts the stop surface FSS.

Figure 45:
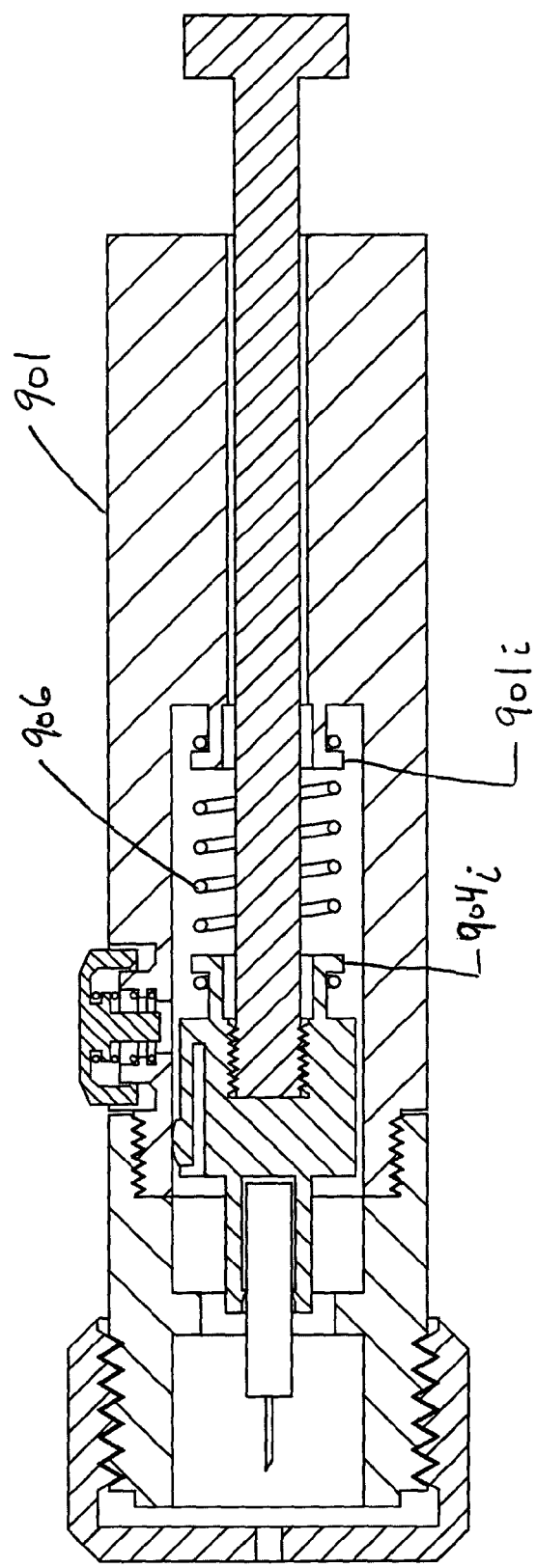
FIG. 45 shows a side cross-section view of still another embodiment of the lancet device. This embodiment is similar to the embodiment shown in FIG. 24, except that the spring has one end that is secured to a flange of the front portion of the lancet holding member and another end secured to a flange of the body.
Figure 46:
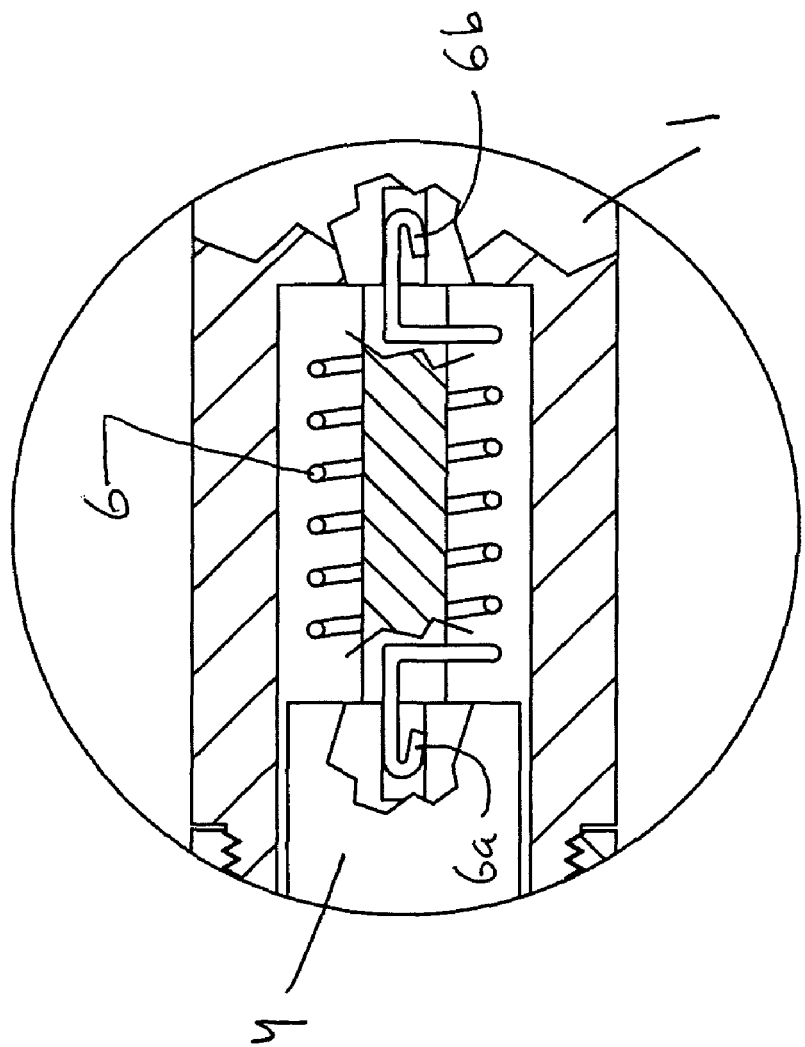
FIG. 46 shows a partial section view of the embodiment shown in FIG. 1 rotated 90 degrees. The attachment of the spring to the front portion and body is shown.

FIG. 45 shows another embodiment of lancet device. Lancet device LD has a lancet body 901 which can be made as a two-piece member as with the embodiment shown in FIGS. 39-40. Alternatively, it can be made as a one-piece structure as in the embodiment shown in, e.g., FIGS. 22-28. Such body parts can, of course, be connected, e.g., using adhesives and/or fasteners and/or welding and/or snap-together holding mechanisms (not shown) to each other when the lancet device LD is initially assembled. The parts other than the body 901 and the front part 904 can be the same as those used in the embodiment shown in FIGS. 22-28. Accordingly, the details of these parts will not be described again. However, the front part 904 in this embodiment may utilize an integrally formed connecting flange 904i for retaining one end of the spring 906. The body 901 may also utilize an integrally formed flange 901i which is connected to another end of the spring 906. The lancet device LD will otherwise function in an manner similar to that of FIGS. 22-28.

FIG. 46 shows one way that spring can be mounted to each of the front part, e.g., 4 and the body, e.g., 1. This arrangement can be used on any of the disclosed embodiments, and especially those of FIGS. 1-28. As can be seen from FIG. 46, the ends 6a and 6b of the spring 6 are shaped with a bend which penetrates openings formed in each of the front part 4 and the body 1. Such frictional engagement can be aided by using, e.g., adhesives, in order to ensure that the spring 6 does not disconnect or disengage from the front part and body.

FIGS. 47-50 shows one possible system for maintaining the depth setting of the front cap. This system can be used on any of the herein disclosed embodiments by modifying the intermediate section to include surface 1002f and ratchet pawl RP. Moreover, the front cap can be modified to include the undulating ratchet surface RS and the groove 1003e. Of course, the invention contemplates other systems or mechanisms for maintaining the depth setting position of the front cap relative to the body.

With reference to FIGS. 47 and 48, the front cap 1003 can have the same outer configuration described with regard to any of the previous embodiments. However, the front cap 1003 can also include axially oriented pointed undulations which form the ratchet surface RS. Although these undulations are in the form of pointed axial projections arranged on an inner circumferential wall, they can also have the form of rounded undulations. The purpose of these undulations or projections/grooves is of course to engage the ratchet pawl RP on the intermediate section 1002. The number of projections/grooves forming the undulations can, of course, be configured to match the desired number of depth settings and/or the desired axial movement of the each setting, i.e., more undulations translates to finer depth settings (with less force generally being required to rotate the front cover 1003) while less undulations translates to move axial distance of the front cover 1003 between discrete depth settings (with more force generally being required to rotate the front cover 1003). Thus, when the front cap 1003 is rotated in either of two opposite directions to change its axial distance relative to the body, the undulating surface will cause the ratchet pawl RP to deflect towards and away from surface 1002f. However, when the front cap 1003 is not rotated, it will automatically be maintained in a position wherein the ratchet pawl RP engages one of the grooves of the undulating surface. Using this system, the user will generally experience a clicking sound as the ratchet pawl RP engages each groove of the undulating surface RS upon rotation of the front cap 1003. In this regard, it is important to ensure that the axial length of surface 1002f is sufficiently long to encompass all of the axial movement of the front cap 1003 between the range of adjustment indicated by the indicia. As can be seen in FIGS. 47 and 48, the surface RS extends from planar surface 1003d to a circumferential groove 1003e.

With reference to FIGS. 49 and 50, the front end of the intermediate section 1002 (or body if no intermediate section is utilized as in the embodiment shown in e.g., FIGS. 14-21) includes one ratchet pawl RP which is integrally formed therewith. Of course, the pawl RP can be replaced with any desired mechanism which deflects towards and away from the surface 1002f such as, e.g., a spring mounted sphere which is embedded in surface 1002f, i.e., between surface 1002f and opening 1002g. The pawl RP includes an arm section that is coupled to the surface 1002f and a rounded end which engages the undulating surface RS. A circumferential space is provided between the arm and the surface 1002f to ensure that the arm can deflect towards the surface 1002f when the pointed portions of the surface RS force the pawl RP towards surface 1002f. While the instant embodiment illustrates a pawl RP arranged in front of the fixed stop wall 1002b, the pawl RP can be arranged in any desired location provided it functions to engage a ratchet surface RS. Additionally, while the drawings illustrate one pawl RP, it should be noted that the invention contemplates using two (oppositely arranged) or more pawls, as desired. Moreover, the invention also contemplates that the pawl RP can be formed or coupled to the front cap 1003 while the ratchet surface RS is formed on the intermediate section 1002 or body.

The various parts, with the exception of the springs, can preferably be made as one-piece structures by e.g., injection molding. In this regard, they are preferably made of a plastic or synthetic resin such as, e.g., ABS plastic. The body and intermediate section can also be made of ABS-Metallic Silver and have a finish designated as SPI-A2. The front cover and back cap may also be made of ABS-Light Blue and have a finish designated as SPI-A2. The end plug, e.g., 413, is preferably made of a plastic or synthetic resin such as, e.g., Delrin plastic. The trigger may also have be made of ABS-Red and have a finish designated as SPI-A2. The holding member may also have be made of Delrin-Natural and have a finish designated as SPI-C1. Of course, other materials and/or finishes may be utilized, without leaving the scope of the invention. Moreover, each part may even be made of a plurality of sections of parts which are joined together to form the complete parts, without leaving the scope of the invention. Thus, all the parts of the lancet device, with the exception of the springs (which can be made of spring steel) and with the exception of the lancet needle (which can be a conventional metal needle mounted to a conventional plastic lancet 10), may be made from plastic materials and can be formed using conventional injection molding techniques or other known manufacturing methods. The front cap and/or body, for example, can be integrally formed with peripheral grooves and/or projections (similar to a coin), and with the indicating marks. However, when practical, other materials and manufacturing processes may also be utilized. Examples of desirable plastics include polypropylene (PP), polyvinyl chloride (PVC), acrylonitrile butadiene styrene (ABS), nylon, linear polyoxymethylene-type acetal resin, e.g., "DELRIN", and polycarbonate (PC), e.g., "LEXAN". The invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A lancet device, comprising:

a body;

a trigger movably mounted to the body;

a front cover removably mounted to the body and comprising a skin engaging end that includes a lancet opening through which a lancet needle may extend;

a holding member movably mounted within the body and comprising a front end and a rear end;

a main spring disposed inside the body between the front and rear ends of the holding member;

the front end being configured to receive a lancet;

a first stop surface that moves with the holding member and being arranged closer to the front end of the holding member than to the rear end of the holding member;

a second stop surface non-movably coupled to the body; and the second stop surface extending inwardly from the body and being arranged closer to a front end of the body than to a rear end of the body and between the first stop surface and the skin engaging end, wherein at least partial rotation of the front cover causes the skin engaging end to move axially relative to the second stop surface, and wherein contact between the first and second stop surfaces defines a puncturing position of the lancet needle.

2. The lancet device of claim 1, further comprising a back cap configured to move between a retracted position and an original position.

3. The lancet device of claim 2, wherein the back cap is configured to move the holding member to a retracted position.

4. The lancet device of claim 2, wherein the back cap is coupled to a surface that engages the rear end of the holding member.

5. The lancet device of claim 2, wherein the back cap includes a surface that engages the rear end of the holding member.

6. The lancet device of claim 5, wherein the back cap comprises an opening that receives a rear end of the holding member.

7. The lancet device of claim 2, wherein the back cap includes a surface that engages projections disposed on the rear end of the holding member.

8. The lancet device of claim 2, further comprising another spring for biasing the back cap towards an original position.

9. The lancet device of claim 1, wherein the main spring biases the holding member towards an extended position, and further comprising another spring for biasing the holding member in an opposite direction.

10. The lancet device of claim 9, wherein said main spring and said other spring are arranged to surround portions of the holding member.

11. The lancet device of claim 9, wherein the main spring is coupled one side of the holding member and to a surface of the body.

12. The lancet device of claim 11, wherein the holding member comprises cylindrical surfaces and a polygonal cross-sectional shape.

13. The lancet device of claim 11, further comprising a locking member mounted to the rear end of the holding member.

14. The lancet device of claim 13, wherein the main spring surrounds a portion of the holding member and wherein the other spring is disposed between a surface of a back cap and the locking member.

15. The lancet device of claim 1, further comprising a mechanism for at least temporarily maintaining a depth setting position of the front cover.

16. The lancet device of claim 1, wherein the holding member comprises an integrally formed deflecting member that engages a surface of the body.

17. The lancet device of claim 1, wherein the front end comprises an opening that is configured to removably receive the lancet.

18. The lancet device of claim 1, further comprising a deflecting member configured to be deflected by the trigger.

19. The lancet device of claim 18, wherein the deflecting member is coupled to the holding member.

20. The lancet device of claim 18, wherein the deflecting member comprises an engaging surface that contacts a surface of the body.

21. The lancet device of claim 20, wherein the deflecting member is integrally formed with the holding member.

22. The lancet device of claim 1, further comprising indicia arranged on at least one of the front cover and the body.

23. The lancet device of claim 22, wherein the indicia is arranged on an outer circumferential surface of the body.

24. The lancet device of claim 22, wherein the indicia is arranged on an outer circumferential surface of the front cover.

25. The lancet device of claim 1, wherein the holding member comprises a front portion that includes the front end and a rear portion that includes the rear end, wherein the front and rear portions are connected together.

26. The lancet device of claim 25, wherein the rear portion comprises a locking end which receives a locking member.

27. The lancet device of claim 26, wherein the front portion comprises a deflecting member configured to be deflected by the trigger.

28. The lancet device of claim 1, wherein the front cover rotates about an axis that runs through the lancet opening and the holding member.

29. The lancet device of claim 1, wherein the main spring is disposed between the trigger and a back cap.

30. The lancet device of claim 1, wherein the body comprises a two-piece body.

31. The lancet device of claim 30, further comprising another spring axially retained between walls of the two-piece body.

32. The lancet device of claim 31, further comprising a back cap movably mounted to the two-piece body.

33. The lancet device of claim 1, wherein the body comprises an ergonomic shape.

34. The lancet device of claim 1, wherein the body comprises cylindrical surfaces.

35. The lancet device of claim 1, wherein the body comprises a plastic material.

36. The lancet device of claim 1, wherein the front cover comprises gripping protrusions.

37. The lancet device of claim 1, further comprising threads connecting the front cover to the body.

38. A method of puncturing a surface of skin using the lancet device of claim 1, the method comprising:
    adjusting a set depth of penetration of the needle by rotating the front cover to a desired set position;
    disposing the skin engaging end of the lancet device against a user's skin; and
    triggering the trigger to cause the lancet needle to penetrate the user's skin,
    wherein the puncture allows a blood sample to be taken.

39. A method of using the lancet device of claim 1, the method comprising:
    rotating the front cover to a desired set position;
    moving the holding member to a retracted position;
    maintaining the holding member in the retracted position until the trigger is triggered;
    disposing the skin engaging end of the lancet device against a user's skin; and
    triggering the trigger to cause movement of the holding member.

40. A lancet device, comprising:
    a body;
    a trigger mounted to the body;
    a removable front cover comprising a skin engaging end that includes a lancet opening through which a lancet needle may extend;
    a holding member movably mounted within the body and comprising a rear end and a front end configured to receive a lancet;
    a wall arranged within the housing and comprising an opening which allows a portion of the holding member to pass therethrough;
    a first spring structured and arranged to move the holding member to an extended position and comprising one end which contacts a portion of the holding member;

a second spring structured and arranged to move the holding member from the extended position to an intermediate position;
a first stop surface arranged on the holding member and being disposed inside the body at a location that is closer to a front end of the body than to a rear end of the body when the holding member is in the intermediate position; and
a second stop surface arranged inside the body and located closer to the front end of the body than to the rear end of the body,
wherein, when the holding member is positioned in a trigger-set position, the front end is arranged on a front side of the wall and the rear end is arranged on back side of the wall, and
wherein contact between the first and second stop surfaces defines the extended position.

41. The lancet device of claim 40, wherein a triggering of the lancet device is cause by movement of the trigger against the biasing force of the trigger spring and by deflection of a deflectable portion of the holding member.

42. The lancet device of claim 40, wherein a triggering of the lancet device is cause by the following:
movement of the trigger; and
deflection of a deflectable portion of the holding member from a position wherein a surface of the deflectable portion contacts a portion of the body to a position wherein the surface of the deflectable portion does not contact the portion of the body.

43. The lancet device of claim 40, wherein a triggering of the lancet device is cause by the following:
movement of the trigger from the initial position to a position wherein a portion of the trigger contacts a deflectable portion of the holding member; and
deflection of the deflectable portion of the holding member from a position wherein a surface of the deflectable portion contacts a portion of the body to a position wherein the surface of the deflectable portion does not contact the portion of the body.

44. A lancet device having depth of penetration adjustment, comprising:
a body comprising a front end and a rear end;
a trigger arranged closer to the front end than to the rear end;
a removable front cover comprising a skin engaging end that includes a lancet opening through which a lancet needle may extend;
a holding member movably mounted within the body and comprising a rear end and a front end configured to receive a lancet;
the holding member comprising a deflecting portion;
the trigger being configured to cause the deflecting portion to disengage from a retaining surface during triggering of the lancet device;
a wall arranged within the housing;
the front end of the holding member being arranged on one side of the wall and the rear end of the holding member being arranged on another side of the wall;
a first spring structured and arranged to move the holding member to an extended position and comprising one end which contacts a portion of the holding member;
a second spring structured and arranged to move the holding member from the extended position to an intermediate position;
a first stop surface arranged on the holding member at a location that is closer to a front end of the body than to a rear end of the body when the holding member is in the intermediate position;
a second stop surface configured to be contacted by the first stop surface and being arranged closer to the front end of the body than to the rear end of the body;
a cocking mechanism structured and arranged to move the holding member to a retracted position when the cocking mechanism is moved toward the rear end of the body;
the cocking mechanism comprising a first portion arranged within the body and a second portion extending out side the body;
the second spring being arranged within the body and being structured and arranged to bias the cocking mechanism toward the front end of the body; and
a depth adjustment mechanism,
wherein contact between the first and second stop surfaces defines the extended position.

45. The lancet device of claim 44, wherein the cocking mechanism is movable along a direction parallel to an axis of the body, wherein the depth adjustment mechanism is configured to rotate relative to the body, wherein the first spring comprises another end which contacts the wall, wherein an axis of the first second spring is axially aligned with an axis of the second spring, and wherein the first and second springs are axially spaced apart and are arranged between the trigger and the rear end of the body.

* * * * *